US012246091B2

(12) United States Patent
Leneweit et al.

(10) Patent No.: US 12,246,091 B2
(45) Date of Patent: Mar. 11, 2025

(54) METHOD OF ENCAPSULATING ACTIVE INGREDIENTS IN LIPOSOMES

(71) Applicant: ABNOBA GMBH, Niefern-Öschelbronn (DE)

(72) Inventors: Gero Leneweit, Niefern-Öschelbronn (DE); Bárbara Santos De Miranda, Pforzheim (DE)

(73) Assignee: ABNOBA GMBH, Niefern-Öschelbronn (DE)

( * ) Notice: Subject to any disclaimer, the term of this patent is extended or adjusted under 35 U.S.C. 154(b) by 1006 days.

(21) Appl. No.: 17/268,003

(22) PCT Filed: Apr. 29, 2019

(86) PCT No.: PCT/EP2019/000133
§ 371 (c)(1),
(2) Date: Feb. 11, 2021

(87) PCT Pub. No.: WO2020/035162
PCT Pub. Date: Feb. 20, 2020

(65) Prior Publication Data
US 2021/0161819 A1    Jun. 3, 2021
US 2022/0000781 A9    Jan. 6, 2022

(30) Foreign Application Priority Data

Aug. 14, 2018  (DE) .................. 10 2018 006 443.4

(51) Int. Cl.
*A61K 9/127*    (2006.01)
*A61K 9/1277*   (2025.01)
(Continued)

(52) U.S. Cl.
CPC ............ *A61K 9/1277* (2013.01); *A61K 31/10* (2013.01); *A61K 38/168* (2013.01); *A61K 47/06* (2013.01);
(Continued)

(58) Field of Classification Search
CPC . A61K 9/1277; B01F 23/4105; B01F 23/413; B01F 23/4145; B01F 29/15
See application file for complete search history.

(56) References Cited

U.S. PATENT DOCUMENTS

2002/0048596 A1* 4/2002 Cevc .................. A61K 9/1271
                                                       424/450
2003/0044999 A1* 3/2003 Singh .................. G01N 21/78
                                                       436/166
(Continued)

FOREIGN PATENT DOCUMENTS

DE   102005002469 B3   5/2006
WO      01/82892 A2   11/2001
WO    2004/071638 A2   8/2004

OTHER PUBLICATIONS

Sophie Pautot et al., "Engineering asymmetric vesicles," The National Academy of Sciences of the USA, vol. 100, No. 19, 10718-10721, Sep. 16, 2003 (4 pages).
(Continued)

*Primary Examiner* — Jacob T Minskey
*Assistant Examiner* — Elisa H Vera
(74) *Attorney, Agent, or Firm* — FLYNN THIEL, P.C.

(57) ABSTRACT

A method for encapsulating active ingredients in liposomes having an active ingredient solution encapsulated with a bilayer composed of two monomolecular layers of amphiphilic compounds comprises:
(a) providing the active ingredient solution;
(b) providing an emulsion by emulsifying the active ingredient solution in a first liquid in the presence of the amphiphilic compound;
(c) providing a liquid phase;
(d) contacting the emulsion with the liquid phase to form a phase boundary; and
(e) centrifuging the emulsion and the liquid phase that are in contact with one another via the phase boundary,
(Continued)

Figure 1:
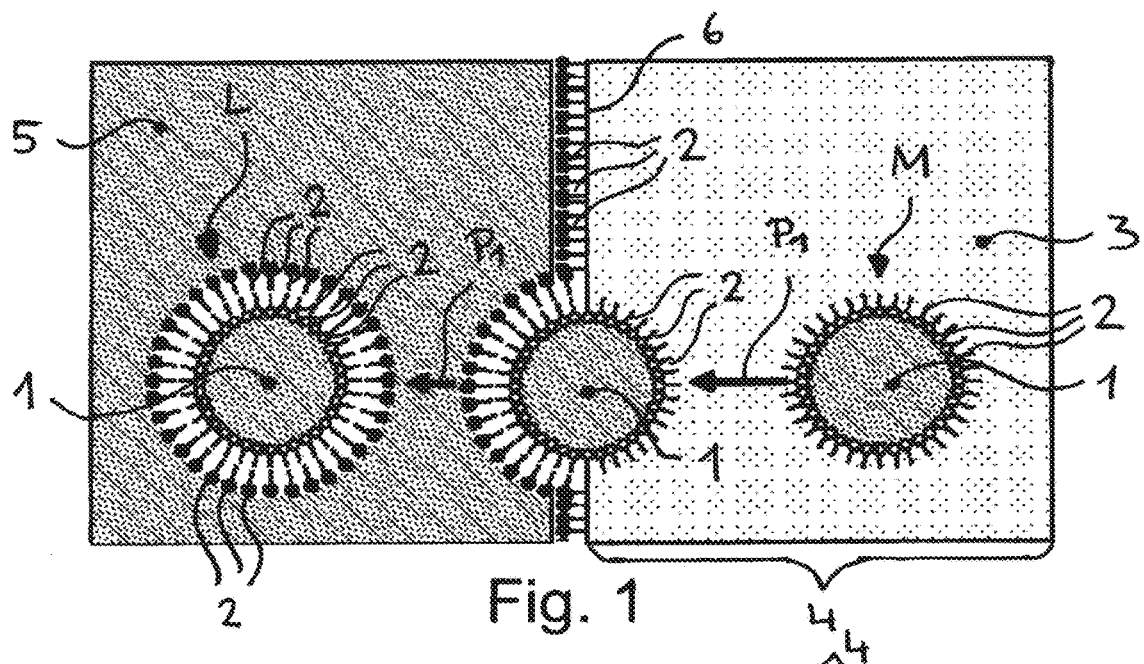

wherein, on passage of the phase boundary, the amphiphilic compound enriched there is added onto the monomolecular inner layer to form a monomolecular outer layer, in order to create the bilayer.

The first liquid of the emulsion is chosen such that the solubility of the amphiphilic compound in the first liquid is not more than $1 \times 10^{-4}$ mol/l.

23 Claims, 2 Drawing Sheets

(51) Int. Cl.
| | |
|---|---|
| *A61K 31/10* | (2006.01) |
| *A61K 38/16* | (2006.01) |
| *A61K 47/06* | (2006.01) |
| *A61K 47/24* | (2006.01) |
| *A61K 47/42* | (2017.01) |
| *B01F 23/41* | (2022.01) |
| *B01F 23/43* | (2022.01) |
| *B01F 29/15* | (2022.01) |
| *B01F 101/22* | (2022.01) |
| *B01J 13/08* | (2006.01) |

(52) U.S. Cl.
CPC .............. *A61K 47/24* (2013.01); *A61K 47/42* (2013.01); *B01F 23/4105* (2022.01); *B01F 23/43* (2022.01); *B01F 29/15* (2022.01); *B01J 13/08* (2013.01); *B01F 23/413* (2022.01); *B01F 23/4145* (2022.01); *B01F 2101/22* (2022.01)

(56) References Cited

U.S. PATENT DOCUMENTS

| | | |
|---|---|---|
| 2003/0124180 A1 | 7/2003 | Ebert et al. |
| 2004/0010060 A1* | 1/2004 | Joanicot .............. C08F 297/026 523/201 |
| 2019/0111022 A1* | 4/2019 | Asano ..................... A61P 35/00 |
| 2021/0330589 A1 | 10/2021 | Leneweit et al. |

OTHER PUBLICATIONS

P. L. Luisi et al., "Organogels from water-in-oil microemulsions," Colloid & Polymer Science 268:356-374 (1990) (19 pages).
International Search Report, with English translation, issued in corresponding International Application No. PCT/EP2019/000133 date of mailing Oct. 2, 2019 (7 pages).
Written Opinion of International Searching Authority, with English translation, issued in corresponding International Application No. PCT/EP2019/000133 date of mailing Oct. 2, 2019 (16 pages).
Ellen Hildebrandt et al., "Liposomal formulations of mistletoe produced by centrifugal technologies and cell proliferation analysis of both mistletoe extracts and isolated mistletoe lectin I," Jan. 1, 2016 (14 pages).
Yogita P. Patil et al., "Novel methods for liposome preparation," Chemistry and Physics of Lipids 177 (2014) 8-18, Nov. 9, 2013 (11 pages).
Massing et al., "Dual asymmetric centrifugation (DAC)—A new technique for liposome preparation," Journal of Controlled Release 125 (2008) 16-24, Elsevier (9 pages).
Maria Laura Immordino et al., "Stealth liposomes: review of the basic science, rationale, and clinical applications, existing and potential," 2006, International Journal of Nanomedicine, vol. 1, 297-315 (Year: 2003) (19 pages).
Mel Dorin et al., "Principles of Continuous Flow Centrifugation," 2015, Beckman Coulter (18 pages).

* cited by examiner

METHOD OF ENCAPSULATING ACTIVE INGREDIENTS IN LIPOSOMES

The invention relates to a method of encapsulating active ingredients in liposomes, comprising
- a solution, especially a hydrophilic solution, of the active ingredient and
- at least one bilayer composed of two at least monomolecular layers of at least one first amphiphilic compound, especially from the group of lipids, wherein the active ingredient solution is encapsulated by the bilayer, comprising the following steps:
(a) providing an active ingredient solution, especially a hydrophilic active ingredient solution, of the active ingredient to be encapsulated by dissolving the active ingredient in at least one solvent, especially a hydrophilic solvent;
(b) providing a first emulsion by emulsifying the active ingredient solution from step (a) in at least one first liquid, especially a hydrophobic first liquid, having zero or sparing miscibility with the at least one solvent of the active ingredient solution, in the presence of the at least one first amphiphilic compound, in order to accumulate an at least monomolecular inner layer of the at least one first amphiphilic compound on the droplets of the active ingredient solution emulsified in the first liquid;
(c) providing a liquid phase, especially a hydrophilic liquid phase, having zero or sparing miscibility with the first liquid of the first emulsion from step (b);
(d) contacting the first emulsion composed of the first liquid and having the droplets of the active ingredient solution that are emulsified therein and have the at least monomolecular inner layer of the at least one first amphiphilic compound that has been accumulated thereon from step (b) with the liquid phase from step (c) to form a phase boundary between the first emulsion from step (b) and the liquid phase from step (c), wherein the at least one first amphiphilic compound is enriched at this phase boundary; and
(e) centrifuging the first emulsion from step (b) and the liquid phase from step (c) that are in contact with one another via the phase boundary, in order to transfer the droplets of the active ingredient solution present in the first emulsion and having the at least monomolecular inner layer of the at least one amphiphilic compound that has been accumulated thereon from the first liquid of the first emulsion from step (b) into the liquid phase from step (c), wherein, when it passes through the phase boundary, the at least one first amphiphilic compound enriched there is accumulated on the at least monomolecular inner layer of the at least one first amphiphilic compound of the droplets of the active ingredient solution to form an at least monomolecular outer layer thereof, in order to produce the bilayer composed of the two at least monomolecular layers of the at least one first amphiphilic compound—and consequently the finished liposomes.

Liposomes, which are also referred to as vesicles, are understood to mean membrane bubbles that may generally be in colloidally suspended form in a hydrophilic, especially aqueous, medium, and enclose a liquid phase, where the liquid phase is typically, albeit not necessarily, a hydrophilic, usually aqueous phase. The membrane shell that encloses the liquid phase is formed from a double layer or bilayer composed of two at least monomolecular layers, composed either of one and the same molecule or of different molecules, each of which have both a nonpolar, i.e. hydrophobic or lipophilic, component and a polar, i.e. hydrophilic or lipophobic, component and are referred to as amphiphilic on account of these properties. The amphiphilic compounds that are used here as membrane-forming molecules are usually lipids, for example phospholipids, sphingolipids, glycolipids, fatty acids or the like, although it is also possible to use other amphiphilic compounds as membrane components, for example lipopolysaccharides, tocopherols, squalenes, sterins or sterols, cholesterols etc. At the time of creation of the bilayer of liposomes, the amphiphilic compounds are arranged in accordance with their hydrophilic/hydrophobic properties, such that the hydrophobic components of the amphiphilic compounds are each directed toward one another, in order to have minimum contact with the phase to be encapsulated, for example hydrophilic or aqueous phase, while the hydrophilic components of the amphiphilic compounds are directed toward the hydrophilic or aqueous phase, for example, within and outside the liposome. On account of the thermodynamic drive to assume an energetically favorable form with a minimum surface area in such an alignment, liposomes typically have an essentially ball-shaped or spherical form. The amphiphilic compounds that form the bilayer(s) of the membrane of liposomes consequently hold together merely by virtue of noncovalent bonding forces, and for that reason the membrane has a primarily fluid character.

Over and above the customary scientific use of the term "liposome" or of the synonymous terms "vesicle", liposomes in the context of the present disclosure also include colloid-chemical aggregates in the form of nanocapsules of any amphiphilic substances, polymer liposomes, lipid nanoparticles and mixtures of such aggregate formations with pure liposomes. Therefore, such colloid-chemical aggregates are always included in the context of the present disclosure, even though only the term "liposome" is used.

The size and exact shape of liposomes depend to a crucial degree on the chemical structure of the amphiphilic compound(s) that form the bilayer(s) of their membrane, and on the physicochemical properties of the typically hydrophilic or aqueous phase to be encapsulated, for example on its ionic strength, pH, osmolality and the like, and the respective production method. Liposomes may either have just a single bilayer, such liposomes being referred to as unilamellar ("unilamellar vesicles", ULV), or they may have multiple bilayers in a respectively concentric arrangement, such liposomes being referred to as multilamellar ("multilamellar vesicles", MLV). The average diameter here is generally between about 20 nm and about 100 μm, especially between about 25 nm and about 30 μm.

As already mentioned, the amphiphilic compounds that form the bilayer(s) of the membrane of liposomes, according to the desired pharmacodynamic profile of action, pharmacokinetic behavior, chemical and physical properties, for example size, size distribution, lamellarity, fluidity, permeability, zeta potential, phase transition temperature of the membrane etc., may be formed from the same or different molecules, for example from the group of lipids, where the bilayer may either have been formed from the same amphiphilic compound or from the same mixtures of multiple amphiphilic compounds, or the individual at least monomolecular layers of the bilayer may each have been formed from different amphiphilic compounds or from mixtures of different amphiphilic compounds. While reference is made in the former case to symmetric liposomes (the at least monomolecular layers of the bilayer of the membrane are of the same structure, but where the molecules of the layers are in opposite alignment with regard to their polar and nonpolar components), reference is made in the latter case to asymmetric liposomes (the at least monomolecular layers of the bilayer of the membrane are of different structure, where the molecules of the layers are again in opposite alignment with regard to their polar and nonpolar components).

While liposomes may also find use, for example, for studies of the biophysical properties of biomembranes, they are used primarily in the cosmetic sector and especially in the medical sector. It is especially possible here, by virtue of the liposomal formulation of active ingredients, such as medicaments and the like, to protect sensitive active ingredients from possible metabolization after application and to specifically lead them to the cells of the organism where the active ingredient is to display its effect, such that any side effects of the active ingredient in a liposomal formulation are reduced and efficacy can be increased, in order to be able to administer lower doses of the active ingredient. Furthermore, the encapsulation of active ingredients in liposomes can increase the plasma half-life. The active ingredient here is typically in the form of a usually hydrophilic, especially aqueous or else alcoholic for example, active ingredient solution in the liposome. Primarily hydrophilic active ingredients may be encapsulated more or less completely in the liposomes, whereas primarily lipophilic substances are more likely to be incorporated into the bilayer of the amphiphilic compound(s).

Accordingly, liposomes play a significant role in modern pharmacy, cosmetics and food technology as transport vehicle for active pharmaceutical or other ingredients, for improvement of skin moisture level or active ingredient absorption, or for high-grade food additives. Further fields of use mentioned merely by way of example for liposomes include drug delivery, synthetic chemistry in general, nanoscale reaction chambers and general technological developments in the fields of energy, optics, electronics, microfluidics, colloid chemistry, biosensors or related fields in which liposomes can be used.

Liposomes may additionally be coated with a polymer layer, for example based on polyethylene glycol (PEG), and/or at least the amphiphilic compound of the outer layer of the bilayer(s) that form(s) the membrane may have been modified with such a polymer, in which case reference is made to "PEGylated liposomes". The polymer layer serves for steric protection of the membrane, and protects and reduces labeling (opsonization) and elimination by the immune system, as a result of which the liposomes can circulate for longer in the organism and be enriched, for example, in tumor tissue. While, as already mentioned above, the pharmacokinetics are influenced by the nature of the liposomes, especially by the amphiphilic compound(s) that form(s) the bilayer(s) of their membrane, and barely at all by the nature of the encapsulated active ingredient itself, drug targeting can be further optimized by PEGylation, which, for tumor therapy, for example, means maximum enrichment of the active ingredients in the tumor tissue. For that reason, many chemotherapeutics are currently administered as liposomal formulations (e.g. DaunoXome®, DepoCyt®, Doxil®/Caelyx® Marqibo®, Mepact®, Myocet®), in order to increase the therapeutic effects through the enrichment in the target tissue, but at the same time to reduce side effects as a result of reduced release in healthy tissue and organs.

Existing commercial production techniques for liposomes are based essentially on the following three alternative methods:

a) the homogenization methods, in which crude liposomes are first produced and these are then brought to a uniform size by mechanical means;
b) detergent dialysis; and
c) the ethanol injection method.

What is common to the methods under the above points b) and c) is that auxiliaries improve the solubility of the amphiphilic compounds that form the bilayer, for example phospholipids, in aqueous solutions, and removal or dilution of the auxiliaries results in formation of the bilayers, which form closed liposomes.

What is common to all the commercial production techniques for liposomes that have been developed to date is that, in the encapsulation, the typically hydrophilic or aqueous or possibly even alcoholic interior is identical to the exterior. Given a customary encapsulation capacity of about 1% to 15%, this means that 99% to 85% of the active ingredient has to be removed subsequently from the exterior and preferably reused. Subsequent remote loading of the liposomes by means of thermal methods or pH gradients is possible only for particular active ingredients and entails other disadvantages, for example reduced storage stability, additional processing steps and the like. Furthermore, a multitude of biogenic active pharmaceutical ingredients, especially proteins, are denatured by these methods.

A further shortcoming of the commercial production methods developed to date is the uniformity of the membrane, i.e. the inside and outside of the bilayer are identical; the liposomes produced are consequently symmetric liposomes. In all naturally occurring biogenic membranes, however, the insides and outsides of the membrane are always different, which is true both with regard to their lipid composition and their protein composition. The asymmetry of biological membranes has an important physiological function for various cellular recognition and transport mechanisms. Accordingly, unlimited manipulability of the composition of the inside and outside of liposome membranes would be desirable, for example for the accumulation of active ingredients on the inside and of steric protective layers or receptors on the outside, which is currently possible to a limited degree only by subsequent processing steps.

It should be pointed out here that the term "monolayer" is typically understood to mean monomolecular layers of amphiphilic or interface-active compounds, for example of lipids, and an emulsion droplet consisting solely of a monomolecular or single layer of an amphiphilic compound or a group of amphiphilic compounds differs from liposomes in that the latter have at least one bilayer of two at least monomolecular layers of amphiphilic compounds, the polar and nonpolar regions of which have mutually opposite orientations in the monolayers that form the bilayer. In addition to this definition, in the context of the present disclosure, the term "monolayer" always also addresses all substances and substance classes capable of forming thin layers, for example polymers and proteins, which is especially also the case when these substance classes and substances, if appropriate, include or may include more than a single molecular layer. Analogously, "bilayer" in the context of the present disclosure is always also understood to mean the combination of two monolayers in the above sense. "Pre-liposomes" in the context of the present disclosure shall be understood to mean emulsion droplets having a monomolecular or single layer of an amphiphilic compound or of a group of amphiphilic compounds.

The option that underlies the invention of synthesizing monolayers from amphiphilic compounds to give a bilayer and dividing them off by means of centrifugal forces to form liposomes is fundamentally known from the prior art.

For instance, H. Träuble and E. Grell: "The formation of asymmetrical spherical lecithin vesicles", Neuroscience Research Program Bulletin, 9, 373-3801 (1971), describes a method of encapsulating active ingredients in liposomes wherein, in a step (a), an aqueous active ingredient solution is provided, which, in a step (b), is dispersed in a phase having zero or sparing miscibility therewith in the presence of one or more amphiphilic compounds in the form of lipids, such that at least one of the amphiphilic compounds accumulates as a monomolecular layer on the emulsified droplets of the active ingredient solution, i.e. forms pre-liposomes in the sense of the present disclosure. Moreover, in a step (c), a phase having zero or sparing miscibility with the continuous phase of the emulsion—an aqueous phase here—is provided, and the pre-liposomes thus produced are transferred from the emulsion to the aqueous phase by centrifugal forces. At the phase transition, the pre-liposomes are surrounded by a second monolayer of at least one of the amphiphilic compounds that has been enriched at the phase boundary, such that the liposome or vesicle is produced to obtain a bilayer. While the method is undoubtedly suitable for production of symmetric liposomes, the supposition is set out in the paper that it is also possible thereby to form liposomes having an asymmetric composition of the bilayer constituted from the various first amphiphilic compounds, but no evidence is supplied as to the implementability of this idea. This is because the unsolved problem in this concept is that the amphiphilic compounds that show the phase boundaries of a) the dispersed droplets and b) the phase boundary between the two immiscible phases cannot be separated from one another. On account of a lack of separation, the amphiphilic compounds can thus reach all interfaces by diffusion, which means that adequate asymmetry of the bilayer cannot be achieved. A further particular problem with this concept lies in the propensity of almost all amphiphilic compounds, for example phospholipids and the like, to form what are called organogels together with an organic phase and an aqueous phase (in this regard see also, for example, P. L. Luisi, R. Scartazzini, G. Haering, P. Schurtenberger: "Organogels from water-in-oil microemulsions", Colloid Polym Sci, 268:356-374 (1990)). These organogels become enriched at the phase boundary between the organic phase and the aqueous phase, and form a barrier layer which becomes increasingly more difficult to overcome and hinders the phase transfer.

A further development of the above-described method of Trauble and Grell is the method according to the paper by S. Pautot, B. J. Frisken, D. A. Weitz: "Engineering asymmetric vesicles", Proceedings of the National Academy of Sciences USA, 100: 10718-10721 (2003a), which is based on the process designed by Trauble and Grell, but extends it with an organic interphase present during the centrifugation step between the emulsion containing the pre-liposomes that have already been provided with a monomolecular layer of at least one amphiphilic compound and the aqueous phase into which the pre-liposomes have been transferred from at least one amphiphilic compound with accumulation of the second monomolecular layer. Although this interphase is miscible with the organic water-in-oil emulsion with the pre-liposomes, it is separable in the centrifugal field on account of its difference in density and contains at least one amphiphilic compound of the outer layer of the bilayer, which is consequently more or less separated from the amphiphilic compound of the inner monolayer. In this way, the interphase gives rise to a sufficient diffusion boundary for the amphiphilic compounds at the interfaces, which makes it possible to form asymmetric bilayers. Here too, however, there is the problem of formation of organogels, especially at this phase boundary between the aqueous phase and the interphase. Moreover, particularly for the reason that the pre-liposomes provided with the (inner) monolayer of at least one amphiphilic compound must pass through the interphase before the (outer) monolayer of the further amphiphilic compound can accumulate, there is the risk of contamination of the liposomes with the organic interphase which is virtually impossible to remove subsequently. Finally, the process according to Pautot et al. is unsuitable for the formation of asymmetric bilayers in which further hydrophilic conjugates, for example polyethylene glycol (PEG), are bonded to the hydrophilic head groups on one side, because, in the method, the amphiphilic compounds that serve for incorporation into the outer monolayer first have to be dissolved in the organic phase, which limits the solubility of conjugates having large hydrophilic molecular components.

Moreover, aside from the unsolved problems described, none of the processes mentioned in the form presented is suitable for employment in a continuous process, in order thus to be able to use it on the industrial scale in an economically viable manner. In principle, the methods are all based on centrifuging a hydrophobic phase together with an aqueous phase. On conclusion of the production process for the liposomes, the two phases should be separated such that the aqueous phase can be utilized as product and the hydrophobic phase as auxiliary for the performance of the process.

It is therefore an object of the invention to provide a method of encapsulating active ingredients in liposomes in a simple and inexpensive manner with at least very substantial avoidance of the aforementioned disadvantages, in that the formation of organogels from the amphiphilic compounds that form the bilayer of the membrane is minimized and it is thus possible to combine two monomolecular layers of amphiphilic compounds to form a bilayer, and continuous production of liposomes should especially be enabled.

In a first aspect of the invention, this object is achieved, in a method of encapsulating active ingredients in liposomes of the type specified at the outset, in that the first liquid of the first emulsion from step (b) is chosen such that the solubility of the at least one first amphiphilic compound in the first liquid is not more than $1 \times 10^{-4}$ mol/l.

The method of the invention consequently envisages that, first of all, in a manner known as such, in a step (a), one or more active ingredient(s) to be encapsulated is/are dissolved in a solvent or in a solvent mixture, in order to produce an active ingredient solution of the at least one active ingredient to be encapsulated. The at least one solvent may, although need not necessarily, especially be a hydrophilic solvent, in which case possible options in practice are primarily physiologically benign water-based solvents including water, for example isotonic solutions, and/or alcohol-based solvents, especially based on ethanol.

In a step (b), this active ingredient solution is then emulsified in a first liquid having zero or sparing miscibility with the at least one solvent or with a mixture of such first liquids in the presence of one or more first amphiphilic compound(s) to obtain a first emulsion, in such a way that an at least monomolecular inner layer of the at least one first amphiphilic compound is accumulated on the droplets of the active ingredient solution emulsified in the first liquid. In this way, pre-liposomes are consequently first produced in the context of the present disclosure, wherein the monomolecular layer of the at least one first amphiphilic compound forms the inner layer of the bilayer of the liposomes to be generated in the subsequent steps. The average droplet size and distribution of this first emulsion and consequently the average diameter of the pre-liposomes or of the liposomes to be produced therefrom can be adjusted in a customary manner, for example by appropriate input of mechanical forces, for example shear forces, in the production of the first emulsion and varied within broad intervals. During a period of a few minutes up to a few hours, the at least one first amphiphilic compound capable of pre-liposome or membrane formation is then able, as the (inner) monolayer, to form by diffusion at the phase boundary between the active ingredient solution droplets and the first liquid of the first emulsion. If the active ingredient solution is a customarily hydrophilic, for example aqueous and/or alcoholic, solution, the first liquid(s) is/are hydrophobic liquid(s) of zero or only very sparing miscibility therewith. The first amphiphilic substance may especially be lipids, for example phospholipids and the like, or any other amphiphilic compounds known for production of liposomes, or mixtures of such compounds, including those of the type specified at the outset.

As well as the provision of this first emulsion with the pre-liposomes composed of droplets of the active ingredient solution enclosed within the inner layer of the at least one first amphiphilic compound, also provided in a step (c) is a liquid phase of zero or sparing miscibility with the first liquid of this first emulsion, i.e. with the continuous phase thereof, where this liquid phase may especially be a hydrophilic phase, provided that the at least one first liquid of the first emulsion containing the pre-liposomes, i.e. the continuous phase thereof, is hydrophobic.

As soon as the (inner) monomolecular layer of the at least one first amphiphilic compound in the first emulsion produced in the above step (b) has reached a minimum density with which it is capable of forming a bilayer, in a subsequent step (d), the first emulsion of the first liquid with the droplets of the active ingredient solution emulsified therein, having the at least monomolecular inner layer of the at least one first amphiphilic compound accumulated thereon, i.e. with the pre-liposomes generated in the above step (b), is contacted with the liquid phase from the above step (c) to form a phase boundary between this first emulsion and this liquid phase, with enrichment of the at least one first amphiphilic compound at this phase boundary.

A concluding step, step (e), finally comprises the centrifuging of the first emulsion from the above step (b) and the liquid phase from the above step (c) that is in contact therewith via the phase boundary in order to convert the droplets of the active ingredient solution that is present in the first emulsion and has the at least monomolecular inner layer of the at least one first amphiphilic compound accumulated thereon, i.e. the pre-liposomes prefabricated in the above manner, from the first liquid of the first emulsion into the liquid phase, wherein, when it passes through the phase boundary, the at least one first amphiphilic compound enriched there is accumulated on the at least monomolecular inner layer of the at least one first amphiphilic compound of the droplets of the active ingredient solution to form an at least monomolecular outer layer thereof, in order to create the bilayer composed of the two at least monomolecular layers of the at least one first amphiphilic compound. The pre-liposomes composed of the droplets of the active ingredient solution with the monomolecular (inner) layer of the first amphiphilic compound accumulated thereon are consequently moved in the centrifugal force field, on account of their difference in density, from the first liquid, especially the hydrophobic liquid, of the first emulsion, i.e. from the continuous phase thereof, to the liquid phase, especially the hydrophilic phase, adjoining the phase boundary via the phase boundary. At this phase boundary, the at least one first amphiphilic compound is, or at least some representatives of multiple first amphiphilic compounds are, then accumulated continuously as monomolecular (outer) layer on the pre-liposomes, in order to form the finished liposomes provided with a bilayer. At the same time, the two at least monomolecular (inner and outer) layers of the at least one first amphiphilic compound approach one another initially with sufficient proximity that they, on account of interactions, especially hydrophobic interactions, between the amphiphilic compounds of the monolayers, form the finished bilayer with a virtually freely adjustable composition of the inner and outer side. Then the encapsulated droplets of the active ingredient solution from the first emulsion, on account of the difference in density, are pushed against the newly formed bilayer with such force that the latter deforms and ultimately surrounds the entire active ingredient solution droplet, which ultimately becomes divided from the bilayer and breaks away from the phase boundary, such that the envelope with a bilayer transforms the active ingredient solution droplet into a liposome.

What has been found in accordance with the invention is that, surprisingly, the formation of organogel, as a result of excess enrichment of the at least one first amphiphilic compound at the phase boundary between the first emulsion and the liquid phase in contact therewith can be prevented in an effective manner in that the first liquid of the first emulsion from the above step (b) is chosen in such a way that the solubility of the at least one first amphiphilic compound in the first liquid is not more than about $1 \times 10^{-4}$ mol/l, preferably not more than about $0.5 \times 10^{-4}$ mol/l, most preferably not more than about $1 \times 10^{-3}$ mol/l, especially not more than about $1 \times 10^{-6}$ mol/l, for example not more than about $1 \times 10^{-7}$ mol/l. According to the invention, there is consequently no formation of a "barrier layer" of the at least one first amphiphilic compound at the phase boundary that could block the phase boundary and hence prevent the formation of liposomes from the active ingredient solution droplets on passage through the phase boundary, such that a high yield of liposomes provided with a bilayer of the at least one first amphiphilic compound is obtained and the efficiency of the method is thus improved to a considerable degree in that the active ingredient solution waste that should be recovered for economic reasons is minimized.

With regard to the fact that impeccable generation of symmetric liposomes is ensured in this way, but the generation of asymmetric liposomes is possible only to a limited degree (cf., in particular, the above remarks in relation to the paper by Trauble et al.), the invention proposes, in a second aspect, a method of producing liposomes which are suitable in the same way both for generation of symmetric liposomes (the first amphiphilic compound(s) is/are identical to the second amphiphilic compound(s)) and more particularly for generation of asymmetric liposomes (the first amphiphilic compound(s) is/are different than the second amphiphilic compound(s)). Such a method of encapsulating active ingredients in liposomes comprising a solution, especially a hydrophilic solution, of the active ingredient and at least one bilayer composed of two at least monomolecular layers of at least one first amphiphilic compound and at least one second amphiphilic compound, especially each from the group of the lipids, wherein the active ingredient solution is encapsulated by the bilayer, comprises the following steps:

(a) providing an active ingredient solution, especially a hydrophilic active ingredient solution, of the active ingredient to be encapsulated by dissolving the active ingredient in at least one solvent, especially a hydrophilic solvent;

(b) providing a first emulsion by emulsifying the active ingredient solution from step (a) in at least one first liquid, especially a hydrophobic first liquid, having zero or sparing miscibility with the at least one solvent of the active ingredient solution, in the presence of the at least one first amphiphilic compound, in order to accumulate an at least monomolecular inner layer of the at least one first amphiphilic compound on the droplets of the active ingredient solution emulsified in the first liquid;

(c) providing a mixture of a liquid phase, especially a hydrophilic phase, having zero or sparing miscibility with the first liquid of the first emulsion from step (b) with the at least one second amphiphilic compound;

(d) contacting the first emulsion composed of the first liquid and having the droplets of the active ingredient solution that are emulsified therein and have the at least monomolecular inner layer of the at least one first amphiphilic compound that has been accumulated thereon from step (b) with the mixture of the liquid phase with the at least one second amphiphilic compound from step (c) to form a phase boundary between the first emulsion from step (b) and the mixture from step (c), wherein the at least one second amphiphilic compound is accumulated at this phase boundary; and (e) centrifuging the first emulsion from step (b) and the mixture from step (c) that are in contact with one another via the phase boundary, in order to transfer the droplets of the active ingredient solution present in the first emulsion and having the at least monomolecular inner layer of the at least one first amphiphilic compound that has been accumulated thereon from the first liquid of the first emulsion from step (b) into the liquid phase of the mixture from step (c), wherein, when it passes through the phase boundary, the at least one second amphiphilic compound enriched there is accumulated on the at least monomolecular inner layer of the at least one first amphiphilic compound of the droplets of the active ingredient solution to form an at least monomolecular outer layer thereof, in order to produce the bilayer composed of the two at least monomolecular layers of the at least one first amphiphilic compound and the at least one second amphiphilic compound—and consequently the finished liposomes.

In the above method, it is thus again the case, at first, in a manner known as such, in a step (a), that one or more active ingredient(s) to be encapsulated are dissolved in a solvent or in a solvent mixture in order to produce an active ingredient solution of the at least one active ingredient to be encapsulated. The at least one solvent in this case may also, albeit not necessarily, especially be a hydrophilic solvent, in which case possible options in practice are primarily physiologically benign water-based solvents including water, or isotonic solutions, and, for example, also alcohol-based solvents, especially based on ethanol.

In a step (b)—in this respect again analogously to the above method—this active ingredient solution is then emulsified in a first liquid having zero or sparing miscibility with the at least one solvent of the active ingredient solution or with a mixture of such first liquids in the presence of one or more first amphiphilic compound(s) to obtain a first emulsion, such that an at least monomolecular inner layer of the at least one first amphiphilic compound is accumulated on the droplets of the active ingredient solution emulsified in the first liquid. In this way, it is again the case that pre-liposomes are first generated in the context of the present disclosure, wherein the monomolecular layer of the at least one first amphiphilic compound forms the inner layer of the bilayer of the liposomes to be generated in the subsequent steps. Because the first emulsion, however, contains only the at least one first amphiphilic compound of the inner monolayer of the bilayer, the formation of pre-liposomes (also) containing the at least one second amphiphilic compound envisaged for the outer monolayer of the bilayer is reliably avoided, such that the greatest possible asymmetry of the bilayer can be achieved merely to that extent. The average droplet size and distribution of this first emulsion and consequently the average diameter of the pre-liposomes or of the liposomes to be generated therefrom may likewise be adjusted in a customary manner, for example by corresponding input of mechanical forces, for example shear forces, in the generation of the first emulsion, and may be varied within broad intervals. During a period of a few minutes up to a few hours, the at least one first amphiphilic compound capable of pre-liposome or membrane formation is then able, as the (inner) monolayer, to form by diffusion at the phase boundary between the active ingredient solution droplets and the first liquid of the first emulsion. If the active ingredient solution is a customarily hydrophilic, for example aqueous and/or alcoholic, solution, the first liquid(s) is/are hydrophobic liquid(s) of zero or only very sparing miscibility therewith. The first amphiphilic substance may again especially be lipids, for example phospholipids and the like, or any other amphiphilic compounds known for production of liposomes, or mixtures of such compounds, including those of the type specified at the outset.

As well as the provision of this first emulsion with the pre-liposomes composed of droplets of the active ingredient solution enclosed within the first layer of the at least one first amphiphilic compound, also provided in a step (c) is a mixture of zero or sparing miscibility with the first liquid of this first emulsion, i.e. with the continuous phase thereof, where this mixture is formed from a liquid phase of zero or sparing miscibility with the first liquid of the first emulsion in the above step (b) with the at least one second amphiphilic compound. In a departure from the prior art method, consequently, what is provided is not just a liquid phase but rather a mixture of such a liquid phase with the at least one second amphiphilic compound which forms the at least monomolecular outer layer of the bilayer of the liposomes to be generated in the subsequent method steps, wherein the at least one second amphiphilic compound is consequently kept spatially separate from the at least one first amphiphilic compound which is present in the first emulsion and forms the at least monomolecular inner layer of the pre-liposomes emulsified therein. Because this mixture contains only the at least one second amphiphilic compound of the outer monolayer of the bilayer, the formation of pre-liposomes (also) containing the at least one first amphiphilic compound intended for the inner monolayer of the bilayer is very substantially avoided, such that, in this respect too, the greatest possible asymmetry of the bilayer can be achieved. The liquid phase of this mixture is again especially a hydrophilic phase if the at least one first liquid of the first emulsion containing the pre-liposomes, i.e. the continuous phase thereof, is hydrophobic or the active ingredient solution is hydrophilic.

As soon as the (inner) monomolecular layer of the at least one first amphiphilic compound in the first emulsion generated in the above step (b) has attained a minimum density with which it will be capable of forming a bilayer at a later stage, in a subsequent step (d), the first emulsion with the droplets of the active ingredient solution emulsified therein having the at least monomolecular inner layer of the at least one first amphiphilic compound accumulated thereon, i.e. with the pre-liposomes generated in the above step (b), is contacted with the mixture of the liquid phase with the at least one second amphiphilic compound from the above step (c) to form a phase boundary between this first emulsion and this mixture, wherein at least the at least one second amphiphilic compound is enriched at this phase boundary. Any enrichment of an excess of the at least one first amphiphilic compound from the first emulsion at the phase boundary as well can be very substantially avoided here in a simple manner by adding the at least one second amphiphilic compound to the mixture in excess and/or adding the at least one first amphiphilic compound to the first emulsion in a proportion corresponding roughly to the proportion capable of being accumulated as the inner monolayer on the droplets of the active ingredient solution that are emulsified there.

A concluding step, step (e), finally again comprises the centrifuging of the first emulsion from the above step (b) and the mixture from the above step (c) that is in contact therewith via the phase boundary in order to convert the droplets of the active ingredient solution that is present in the first emulsion and has the at least monomolecular inner layer of the at least one first amphiphilic compound accumulated thereon, i.e. the pre-liposomes prefabricated in the above manner in the context of the present disclosure, from the first liquid of the first emulsion into the liquid phase of the mixture, wherein, when it passes through the phase boundary, the at least one second amphiphilic compound enriched there is accumulated on the at least monomolecular inner layer of the at least one first amphiphilic compound of the droplets of the active ingredient solution to form an at least monomolecular outer layer thereof, in order to create the bilayer composed of the two at least monomolecular layers of the at least one first and second amphiphilic compounds. The pre-liposomes composed of the droplets of the active ingredient solution with the monomolecular (inner) layer of the at least one first amphiphilic compound accumulated thereon are consequently moved in an analogous manner in the centrifugal force field, on account of their difference in density, from the first liquid, especially the hydrophobic liquid, of the first emulsion, i.e. from the continuous phase thereof, to the liquid phase, especially the hydrophilic phase, adjoining the phase boundary via the phase boundary. At this phase boundary, the at least one second amphiphilic compound is then accumulated continuously as monomolecular (outer) layer on the pre-liposomes, in order to form the finished liposomes provided with a bilayer. In this case too, the two at least monomolecular (inner and outer) layers of the at least one first amphiphilic compound and the at least one second amphiphilic compound approach one another initially with sufficient proximity that they form the finished bilayer with virtually freely adjustable composition of the inner and outer faces on account of interactions, especially hydrophobic interactions, between the same first and second amphiphilic compounds of the monolayers (if symmetric liposomes are to be generated) or especially different first and second amphiphilic compounds of the monolayers (if asymmetric liposomes are to be generated). Then the encapsulated droplets of the active ingredient solution from the first emulsion, on account of the difference in density, are pressed against the newly formed bilayer with sufficient force that the latter is deformed and ultimately surrounds the entire active ingredient solution droplet, which ultimately becomes divided from the bilayer and breaks away from the phase boundary, such that the envelope with a bilayer transforms the active ingredient solution droplet into a liposome. If the at least one second amphiphilic compound used here is a compound other than the at least one first amphiphilic compound, it is possible in a simple manner to generate asymmetric liposomes having a different structure of the inner and outer, at least monomolecular layer of their bilayer.

For the sake of completeness, it should be pointed out here that what is being addressed by "of zero or sparing miscibility" in relation to the (hydrophilic) active ingredient solution with the (hydrophobic) first liquid of the first emulsion or in relation to the (hydrophobic) first liquid of the first emulsion with the (hydrophilic) liquid phase or with the mixture of the (hydrophilic) liquid phase and the at least one second amphiphilic compound is sufficiently sparing miscibility that leads to formation of a phase boundary on combination of the aforementioned components.

In order to effectively prevent the formation of an organogel, especially of the at least one first amphiphilic compound, as a result of enrichment of the at least one first amphiphilic compound at the phase boundary between the first emulsion and the liquid phase of the mixture that is in contact therewith with the at least one second amphiphilic compound in this case too, what is envisaged by the invention in this case too, in an analogous manner, is that the first liquid of the first emulsion according to step (b) above is chosen in such a way that the solubility of the at least one first amphiphilic compound in the first liquid is not more than about $1 \times 10^{-4}$ mol/l, preferably not more than about $0.5 \times 10^{-4}$ mol/l, most preferably not more than about $1 \times 10^{-3}$ mol/l, especially not more than about $1 \times 10^{-6}$ mol/l, for example not more than about $1 \times 10^{-7}$ mol/l. What is consequently formed in this case too is not a "barrier layer" composed of the at least one first amphiphilic compound at the phase boundary, such that a high yield of liposomes provided with a bilayer of the at least one first amphiphilic compound is obtained and the efficiency of the process is considerably improved in that the active ingredient solution waste, which should be recovered for economic reasons, is minimized.

In order also to prevent excessive enrichment of the at least one second amphiphilic compound at the aforementioned phase boundary and consequently the formation of an organogel therefrom, it may additionally be a particular option for the first liquid of the first emulsion in step (b) to be chosen such that the solubility both of the at least one first amphiphilic compound and of the at least one second amphiphilic compound in the first liquid is not more than about $1 \times 10^{-4}$ mol/l, preferably not more than about $0.5 \times 10^{-4}$ mol/l, most preferably not more than about $1 \times 10^{-3}$ mol/l, especially not more than about $1 \times 10^{-6}$ mol/l, for example not more than about $1 \times 10^{-7}$ mol/l.

In an advantageous further development of the process of the aforementioned type which is suitable both for production of symmetric and especially for production of asymmetric liposomes, it may be the case that the mixture of the liquid phase, especially the hydrophilic liquid phase, with the at least one second amphiphilic compound used in step (c) is a second emulsion of the liquid phase and at least one second liquid, especially a hydrophobic second liquid, having zero or sparing miscibility therewith with the at least one second amphiphilic compound, in that the second liquid is emulsified in the liquid phase in the presence of the at least one second amphiphilic compound in order to accumulate an at least monomolecular layer of the at least one second amphiphilic compound on the droplets of the second liquid emulsified in the liquid phase and to immobilize the second amphiphilic compound on these droplets in this way; and on centrifugation of the first emulsion from step (b) and the mixture in the form of the second emulsion from step (c) that are in contact with one another via the phase boundary, the droplets of the second liquid with the at least monomolecular layer of the at least one second amphiphilic compound accumulated thereon are constantly transferred from the liquid phase of the second emulsion to the phase boundary between the first emulsion and the second emulsion, in order to constantly enrich the at least one second amphiphilic compound at this phase boundary.

Rather than a mere mixture or suspension of the at least one second amphiphilic compound with the liquid phase from step (c), what is used is consequently a second emulsion, in that the liquid phase, especially the hydrophilic liquid phase, of this mixture is emulsified with the at least one second liquid, especially hydrophobic second liquid, of zero or sparing miscibility therewith. In this way, it is possible to produce emulsion droplets in the second emulsion—in a corresponding manner to that in the first emulsion—formed from the droplets of the second liquid emulsified in the liquid phase and an at least monomolecular layer of the at least one second amphiphilic compound accumulated thereon. The at least one second amphiphilic compound may be immobilized in this way and is consequently no more or less free in a mere mixture or suspension. If this second emulsion is contacted in step (d) with the first emulsion to form a phase boundary between the continuous phases thereof, the subsequent centrifugation of the first and second emulsions according to step (e) transfers the droplets of the second liquid with the at least monomolecular layer of the at least one second amphiphilic compound accumulated thereon from the liquid phase of the second emulsion constantly to the phase boundary between the first emulsion and the second emulsion, such that excessive enrichment of the at least one second amphiphilic compound, let alone the formation of an organogel therefrom, at the phase boundary can be reliably avoided because the at least one second amphiphilic compound immobilized on the emulsified droplets of the second liquid is supplied constantly to the phase boundary in this way and is continuously enriched at this phase boundary, in order to accumulate on the inner layer when the droplets of the active ingredient solution with the at least monomolecular (inner) layer of the at least one first amphiphilic compound accumulated thereon pass through the phase boundary as the outer layer and to form the bilayer. Furthermore, it is possible in this way to keep the first and second amphiphilic compounds ideally separated from one another (each amphiphilic compound is accumulated and consequently immobilized on emulsion droplets of the first and second emulsions that are in contact with one another solely via the phase boundary), such that highly asymmetric liposomes can be produced if the second amphiphilic compound(s) is/are chosen differently than the first amphiphilic compound(s).

The droplets of the second liquid, especially the hydrophobic second liquid, emulsified in the second emulsion and having the at least monomolecular layer of the at least one second amphiphilic compound accumulated thereon are also referred to hereinafter, for the sake of simplicity, as "amphiphile carriers".

The second liquid, especially the hydrophobic second liquid, which has zero or sparing miscibility with the liquid phase, especially the hydrophilic liquid phase, of the second emulsion, which forms the "core" of the amphiphile carrier in the context of the present disclosure with the at least one second amphiphilic compound accumulated thereon, may advantageously be chosen to correspond to the first liquid, especially the hydrophobic first liquid, of the first emulsion from step (b) that forms the continuous phase of the first emulsion. If the first liquid, accordingly, corresponds to the second liquid, this can be recovered without difficulty in a composition that is always constant after, during the centrifuging, the amphiphile carrier from the second liquid and the at least one second amphiphilic compound accumulated thereon have reached the phase boundary between the first emulsion and the second emulsion, the second amphiphilic compound is enriched at the phase boundary and has been accumulated as outer layer on the pre-liposomes composed of the active ingredient solution with the at least one first amphiphilic compound accumulated thereon, and the droplets of the second liquid of the second emulsion have been transferred through the phase boundary into the same first liquid.

The mixture in the form of the second emulsion with the at least one second amphiphilic compound immobilized on the amphiphile carriers according to step (c) may preferably be produced by first providing a mixture of the liquid phase from step (c) and the at least one second amphiphilic compound; and then emulsifying the second liquid in this mixture to form the second emulsion, by dispersing the second liquid into this mixture.

In this way, amphiphile carriers in the sense of the present disclosure are formed in a reliable and reproducible manner from the at least one second amphiphilic compound already present in the mixture of the liquid phase, especially the hydrophilic liquid phase, when the second liquid, especially the hydrophobic second liquid, is dispersed into this mixture and the second amphiphilic compound accumulates on the droplets thereof.

In a corresponding manner, the first emulsion can advantageously be produced in step (b) by first providing a mixture of the active ingredient solution of the active ingredient to be encapsulated from step (a) and the at least one first amphiphilic compound; and then emulsifying this mixture to form the first emulsion from step (b) in the first liquid by dispersing the mixture into the first liquid.

For the homogeneity of the size of the liposomes, the size distribution of the first emulsion may be adjusted here by appropriate mechanical comminution. For the minimization of the size of the active ingredient solution droplets and the optimization of the monodispersity thereof, and consequently of the liposomes, it may be advantageous when mechanical comminution methods are employed either continuously or cyclically in order to compensate for the input of energy by temperature control. The same applies to any production of the second emulsion (see above).

As already mentioned, in the selection of the first liquid, especially the hydrophobic first liquid, of the first emulsion from step (b), it should be taken into account in accordance with the invention that the solubility of the at least one first amphiphilic compound and preferably also of the at least one second amphiphilic compound should be not more than about $1 \times 10^{-3}$ mol/l, such that the formation of organogel structures at the phase boundary between the first liquid of the first emulsion and the liquid phase, especially the hydrophilic liquid phase, or the mixture of the liquid phase, especially the hydrophilic liquid phase, and the at least one second amphiphilic compound or the second emulsion is reliably avoided. If the active ingredient solution has a hydrophilic character and is in aqueous and/or alcoholic form, for example, as is typically the case, the first liquid used in the first emulsion in step (b) may appropriately be a hydrophobic liquid especially selected from the group of the liquid, partly or wholly halogenated hydrocarbons, including the fluorocarbons,
silicone oils and
siloxanes, including mixtures thereof, in which, in particular, virtually all amphiphilic lipids have the only very low solubility in accordance with the invention. Fluorinated or perfluorinated oils, i.e. fluorocarbons, are phases that are virtually immiscible with water or other hydrophilic liquids, all of which provide the properties needed for implementation of the method of the invention, such as with regard to a different, especially elevated, density relative to aqueous and alcoholic media, a low(er) freezing point (than aqueous and alcoholic media), a relatively low viscosity and, indeed, especially the avoidance of gel-forming interactions with amphiphilic compounds including lipids and a hydrophilic, for example aqueous and/or alcoholic, phase. The same applies to silicone oils, which addresses polymerized siloxanes with organic side chains in liquid form, and to siloxanes in liquid form, which addresses compounds having the general structure

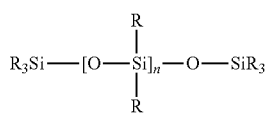

where each "R" is a hydrogen atom or an alkyl group and "n" is a natural number.

It is consequently not only in this case that the solvent used in the active ingredient solution in step (a) is preferably a hydrophilic solvent, especially a water-based hydrophilic solvent, including water, for example isotonic solutions, and/or an alcohol-based hydrophilic solvent, especially based on ethanol or glycerin, or glycerol.

In one development of the invention, it may be the case that the first liquid, especially hydrophobic first liquid, of the first emulsion with the droplets of the active ingredient solution, especially the hydrophilic active ingredient solution, emulsified therein and having the at least monomolecular inner layer of the at least one first amphiphilic compound accumulated thereon from step (b) is chosen such that it has a lower melting point than the active ingredient solution;
the first emulsion from step (b) is cooled down to a temperature between the melting point of the first liquid, especially the hydrophobic first liquid, of the first emulsion and the melting point of the active ingredient solution, especially the hydrophilic active ingredient solution, in order to convert the droplets of the active ingredient solution emulsified in the first liquid and having the at least monomolecular inner layer of the at least one first amphiphilic compound accumulated thereon from step (b) into the solid state; and then
the first emulsion from step (b) in the solid state of the droplets of the active ingredient solution is contacted with the
liquid phase or
mixture of the liquid phase with the at least one second amphiphilic compound
that has zero or sparing miscibility with the first liquid, especially the first hydrophobic liquid, of the first emulsion from step (b), to form the phase boundary according to step (d), and the first emulsion from step (b) and
the liquid phase or
the mixture of the liquid phase with the at least one second amphiphilic compound
that are in contact with one another via the phase boundary are centrifuged in step (e).

It is advantageously an option here for the active ingredient solution, especially the hydrophilic active ingredient solution, having the at least monomolecular inner layer of the at least one first amphiphilic compound accumulated thereon to be kept in the solid state during the centrifuging, in order to move it, on account of a resultant (additional) difference in density, from the phase boundary in the direction of the, in particular hydrophilic,
liquid phase or
mixture of the liquid phase with the at least one second amphiphilic compound.

Consequently, the first emulsion is preferably cooled to such a degree as to freeze the active ingredient solution droplets, for example aqueous and/or alcoholic active ingredient solution droplets, but to leave the first liquid, especially the hydrophobic first liquid, surrounding it, i.e. the continuous phase of the first emulsion, still in liquid form. This may contribute to prevention of excessive or even complete deformation of the active ingredient solution droplets with the (inner) at least monomolecular layer of the at least one first amphiphilic compound accumulated thereon, without penetrating the phase boundary and hence in turn forming a barrier layer at the phase boundary. If, more particularly, a first liquid, especially a hydrophobic first liquid, which is heavier than the aqueous and/or alcoholic active ingredient solution droplets, for example, is chosen, the frozen active ingredient solution droplets, as a result of centrifugal forces, not only move more easily or quickly within the first liquid of the first emulsion but also in the liquid phase, especially the hydrophilic liquid phase, or in the mixture of the liquid phase with the at least one second amphiphilic compound or in the second emulsion, after they have passed through the phase boundary and the enveloping with a bilayer to form the finished liposomes has taken place, because the frozen active ingredient solution droplets have a lower density than the unfrozen liquid phase, especially the hydrophilic unfrozen liquid phase, or than the mixture of the unfrozen liquid phase with the at least one second amphiphilic compound, where this liquid phase, just like the solvent of the active ingredient solution droplets, may especially be in aqueous or alcoholic form or in the form of water. For this purpose, at least the first emulsion should be at a temperature slightly below the freezing point of the active ingredient solution droplets in order that they remain frozen in the surrounding first liquid of the first emulsion.

As already mentioned, the active ingredients incorporated into a liposome are protected against the destructive effect of enzymes and from premature secretion from the body by the bilayer composed of amphiphilic compounds, such as in the form of a bilayer composed of the same or different lipids, on the way to its intended site in the organism. In some pharmaceutical products, however, the liposomes must also be protected by a surface polymer layer, typically formed on the basis of polyethylene glycol (PEG), in order to prevent opsonization and phagocytosis by immune cells, for example in the liver, before the active ingredient has reached its intended site. With the aid of extraneous molecules, for example antibodies, that become attached to the outside of the liposomes, it is additionally possible to attempt to precisely determine the intended site of the active ingredient by binding to a specific receptor ("drug targeting"). It is thought here that liposomes, on account of their cell membrane-like chemical characteristics, are fused relatively easily to the cell membrane or, after pinocytosis or endocytosis, to the endosomal and lysosomal membrane, and then release their contents into the cell interior. Accordingly, in an advantageous development of the method of the invention, it may be a case that the bilayer consisting of.

the two at least monomolecular layers of the at least one first amphiphilic compound or.

the two at least monomolecular layers of the at least one first amphiphilic compound and of the at least one second amphiphilic compound, especially exclusively the outer at least monomolecular layer of the bilayer, is modified by reaction with hydrophilic polymer conjugates. This may firstly be accomplished, for example, by modifying the ready-produced liposome in such a way that such polymer conjugates are accumulated on the at least monomolecular outer layer of the bilayer, for example by means of electrostatic charging thereof. Especially the method of the invention can open up the option of using at least one second amphiphilic compound, for example in the form of lipids, to which the polymer conjugates have already been bound beforehand for the at least monomolecular outer layer of the bilayer.

Furthermore, the method of the invention may be performed batchwise in a batchwise centrifugation device, for example batchwise using conventional centrifuge tubes;

semicontinuously in a batchwise centrifugation device, for example likewise batchwise, but with supply of the first emulsion and of the liquid phase having zero or sparing miscibility therewith, or of the mixture or second emulsion, over a period of time; or especially also continuously in a flow-operated, continuous centrifugation device.

In the case of batchwise performance of the method in a batchwise centrifugation device, it may be the case, for example, that firstly the first emulsion from step (b) and secondly the liquid phase or mixture or second emulsion from step (c) is supplied to the centrifugation device, and then centrifuged, after which firstly the liquid phase comprising the liposomes provided with the bilayer composed of the two at least monomolecular layers of the amphiphilic compound(s) and secondly the first liquid are withdrawn from the centrifugation device. In the case of semicontinuous performance of the method in a batchwise centrifugation device, it may be the case that, for example, firstly the first emulsion from step (b) and secondly the liquid phase or mixture or second emulsion from step (c) are supplied continuously to the centrifugation device over a period of time, during which they are centrifuged, and then firstly the liquid phase comprising the liposomes provided with the bilayer composed of the two at least monomolecular layers of the amphiphilic compound(s) and secondly the first liquid are withdrawn from the centrifugation device. As elucidated in detail further down with reference to the drawings, it may additionally especially be the case, in the case of continuous performance of the method in a flow-operated continuous centrifugation device, that firstly the first emulsion from step (b) and secondly the liquid phase or mixture or the second emulsion from step (c) are supplied continuously to the centrifugation device and centrifuged, and firstly the liquid phase comprising the liposomes provided with the bilayer composed of the two at least monomolecular layers of the amphiphilic compound(s) and secondly the first liquid are withdrawn continuously from the centrifugation device.

The method of the invention—whether for production of symmetric or for production of asymmetric liposomes—offers a novel means of producing liposomes in a technically relatively simple and inexpensive manner, these being equally suitable especially for therapeutic use, but additionally also for all other known uses of liposomes, for example in the field of foods or else of cosmetics for personal care. The arrangement of different, at least monomolecular monolayers at the phase boundary between the first emulsion, such as a "water-in-oil emulsion", and a second emulsion, such as an "oil-in-water emulsion", also allows combination of these two monolayers by hydrophobic interactions between, for example, fatty acid chains to form a stable bilayer with different properties of the later inner or outer layer of a liposome, with freely adjustable substance composition of the inner and outer, at least monomolecular layers of the bilayer, which opens up new options for the functionality of liposome preparations. In addition, the production process enables high encapsulation efficiency, since the production of an emulsion in an immiscible surrounding phase enables complete enclosure of the active ingredient in the emulsion droplets. In the enveloping of the emulsion droplets with a second monolayer for the encapsulation of active ingredients into the liposome newly produced thereby, only small losses of the active ingredient occur in the region surrounding the liposome after production thereof, such that it is possible to achieve a high utilization rate of the typically costly active ingredients. By virtue of the volume ratio of hydrophilic and hydrophobic phase and the quantitative ratio of membrane-forming amphiphilic compounds, for example in the form of phospholipids, it is possible to create the prerequisites for the formation of liposomes in the desired size and concentration, where an appropriate excess of amphiphilic compounds should advantageously be provided in order that a sufficient interface density of amphiphilic compounds at the phase boundary is established, but this does not result in the formation of an organogel in accordance with the invention.

Figure 2:
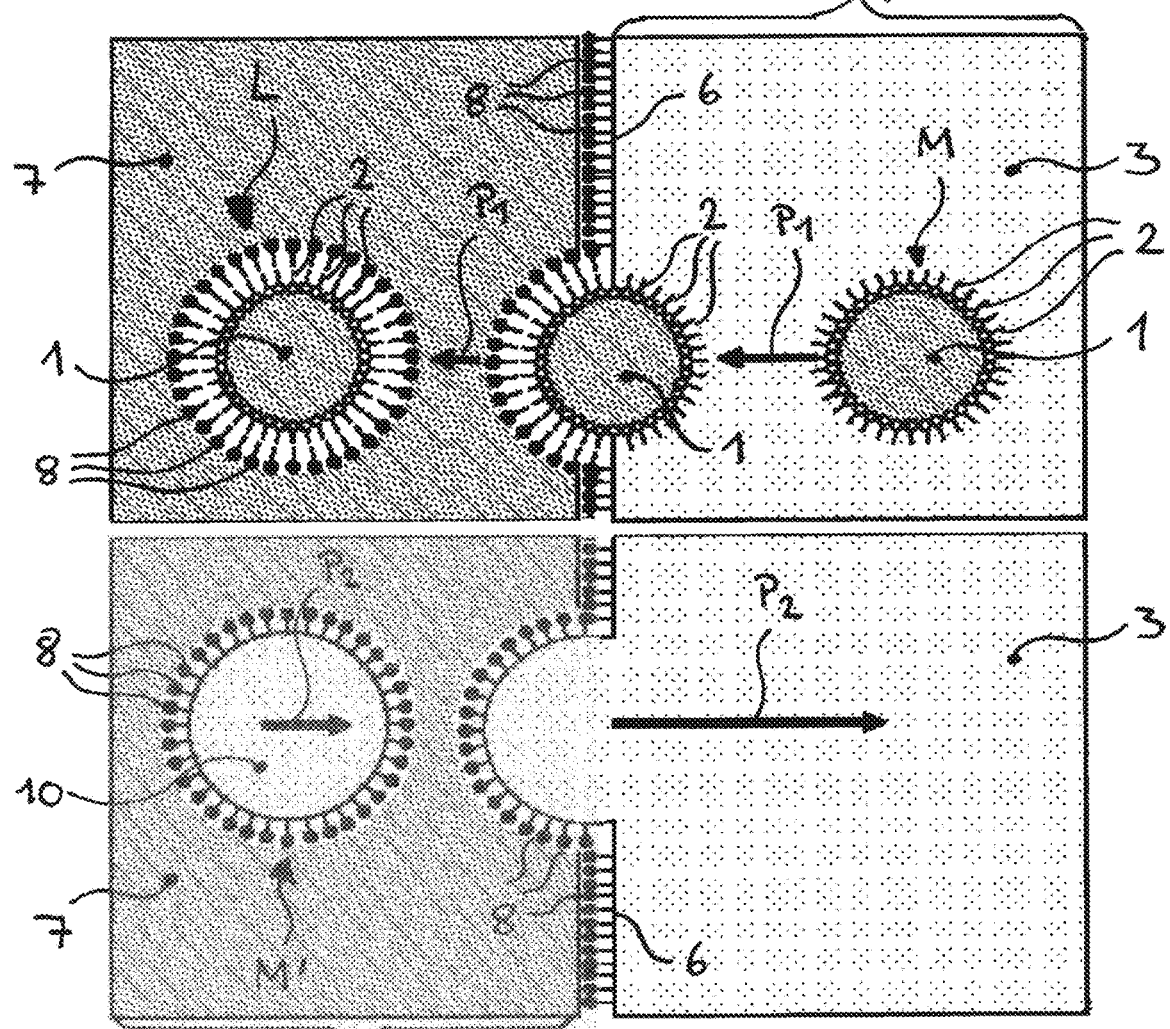
Figure 3:
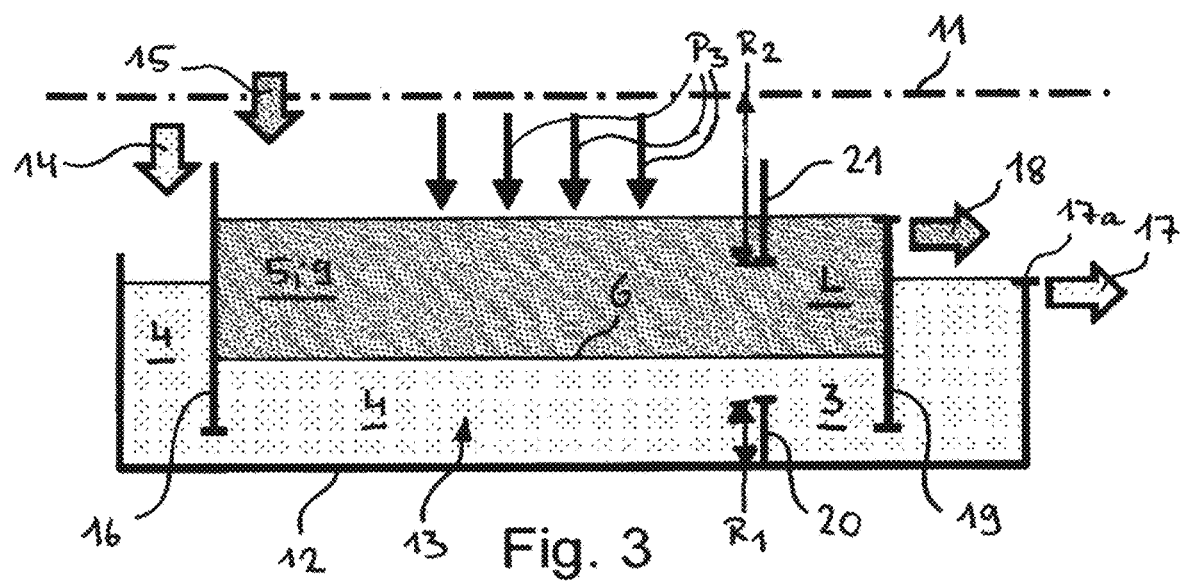
Figure 4:
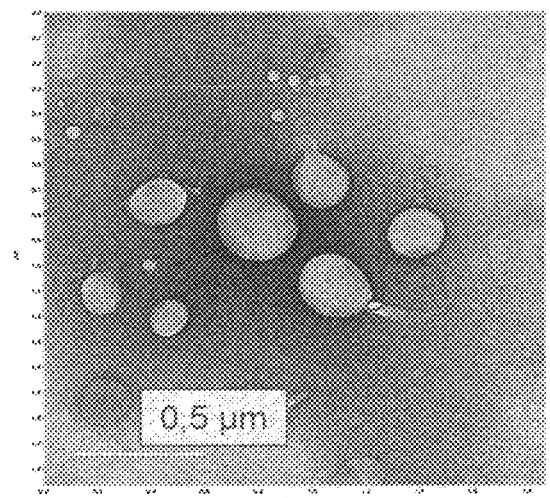
Figure 5:
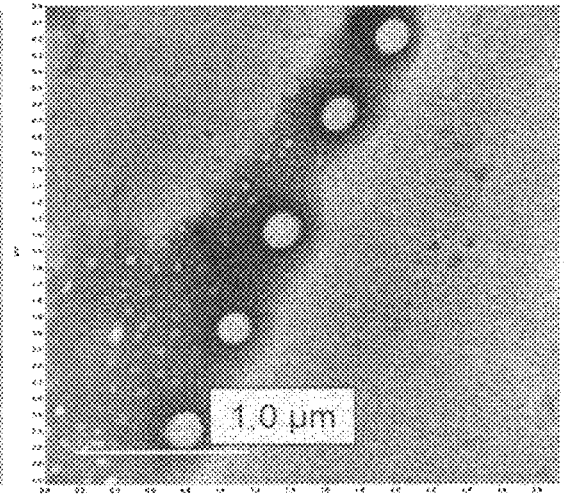
Figure 6:
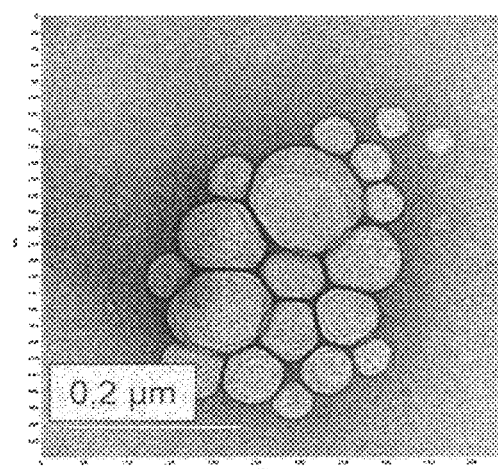

Further features and advantages of the invention will be apparent from the description that follows of working examples with reference to the drawings. The drawings show:

FIG. 1 a highly schematized view for illustration of the production of essentially symmetric liposomes by means of a first embodiment of a method of the invention for encapsulation of active ingredients in liposomes;

FIG. 2 a highly schematized view for illustration of the production of essentially asymmetric liposomes by means of a second embodiment of a method of the invention for encapsulation of active ingredients in liposomes;

FIG. 3 a schematic cross-sectional view of half the cross section of an embodiment of a centrifuge device for continuous performance of a method of encapsulation of active ingredients in liposomes;

FIG. 4 a transmission electron micrograph of symmetric liposomes composed of an active ingredient solution of 10 µg/ml of the mistletoe extract viscumin in 15 mM aqueous phosphate buffer, encapsulated in a bilayer of the lipid dipalmitoylphosphatidylcholine (DPPC), produced according to working example 1;

FIG. 5 a transmission electron micrograph of symmetric liposomes composed of an active ingredient solution of 10 µg/ml the mistletoe extract viscumin in 15 mM aqueous phosphate buffer, encapsulated in a bilayer of the lipid distearoylphosphatidylcholine (DSPC), produced according to working example 2; and FIG. 6 a transmission electron micrograph of symmetric liposomes composed of an active ingredient solution of 10 µg/ml of the mistletoe extract viscumin in 15 mM aqueous phosphate buffer, encapsulated in a bilayer composed of the lipids dioleoylphosphatidylcholine (DOPC) and cholesterol in a molar ratio of 60:40, prepared according to working example 3.

FIG. 1 shows a situation during the formation of primarily symmetric liposomes in a first embodiment of a method of the invention for encapsulation of active ingredients in liposomes L by an enlarged detail view in a highly schematized manner. What can be seen in the right-hand section of FIG. 1 is a droplet, for example with a diameter between about 0.1 μm and about 200 μm, of an active ingredient solution 1, which has been produced by dissolving the active ingredient beforehand according to step (a) in a solvent. The solvent in the present case is, for example, a hydrophilic water- and/or alcohol-based solvent.

As additionally apparent in the right-hand section of FIG. 1, a monomolecular (inner) layer of a first amphiphilic compound 2, for example a lipid, has accumulated on the droplets of the active ingredient solution 1 to form a pre-liposome M, wherein the polar regions of the first amphiphilic compound 2 have become aligned in the direction of a hydrophilic active ingredient solution 1, and the nonpolar regions have become aligned in the direction of a first liquid 3—hydrophobic here—that has zero or only sparing miscibility with the solvent surrounding the droplets of the active ingredient solution 1. For production of a first emulsion 4 in this form, the disperse phase of which is formed by the droplets of the hydrophilic active ingredient solution 1 and the continuous phase of which by the hydrophobic first liquid 3, a mixture of the active ingredient solution 1 and the first amphiphilic compound 2, for example, has first been provided beforehand in step (b), and then this mixture has been dispersed into the first liquid 3 to obtain the first emulsion 4. The—hydrophobic—first liquid 3, which, in the present case, is a liquid halogenated hydrocarbon, for example, in the form of one or more fluorocarbons, has been chosen such that the solubility of the first amphiphilic compound 2 is less than $10^{-4}$ mol/l—here, less than $10^{-3}$ mol/l (see further details below). In addition, the first liquid 3 has preferably also been selected in such a way that it has a lower melting point than the active ingredient solution 1 emulsified in the first emulsion 4 (likewise, see further details below). The—hydrophobic—first liquid 3 also has a different density than the active ingredient solution 1, where the fluorocarbon used in the present case has a higher density than the aqueous and/or alcoholic active ingredient solution 1. At the same time, it is of course also possible in principle to use a "lighter" first liquid 3 compared to the active ingredient solution 1, i.e. one having a lower density by comparison.

As apparent from the left-hand section of FIG. 1, it is additionally possible for a liquid phase 5—hydrophilic here—having zero or sparing miscibility with the first liquid 3 of the first emulsion 4 to have been provided in step (c), which, for example, may be chosen to correspond to the solvent of the active ingredient solution 1 and consequently may, for example, likewise be aqueous and/or alcoholic.

As additionally apparent from the two sections of FIG. 1, the first emulsion 4 composed of the first hydrophobic liquid 3 comprising the pre-liposomes M composed of the droplets of the active ingredient solution 1 emulsified therein and having the monomolecular (inner) layer of the first amphiphilic compound 2 accumulated thereon from step (b) has been contacted with the liquid hydrophilic phase 5, followed by formation of a phase boundary 6 between the first liquid 3, i.e. the continuous phase of the first emulsion 4, and the liquid phase 5 on account of their sparing miscibility with one another. The first amphiphilic compound 2 which has typically been added in excess to the first emulsion 4 for this purpose has been enriched here at this phase boundary 6, and, on account of the low solubility thereof in accordance with the invention in the first liquid 3 of the first emulsion 4, there has nevertheless been no formation of an organogel as a result of excessive accumulation of the first amphiphilic compound 2 at the phase boundary 6; instead, it takes up only one or a few molecular layers.

Step (e) of the method, finally, envisages centrifugation of the first emulsion 4 and the liquid phase 5 that are in contact with one another via the phase boundary 6, in order to transfer the droplets of the active ingredient solution 1 that are present in the first emulsion 4 and comprise the monomolecular inner layer of the first amphiphilic compound 2 accumulated thereon in the direction of the arrow $P_1$ from the first liquid 3 of the first emulsion 4 through the phase boundary 6 with the molecules of the first amphiphilic compound 2 enriched thereon into the liquid phase 5, wherein, when it passes through the phase boundary 6, the first amphiphilic compound 2 is accumulated at the monomolecular inner layer of the first amphiphilic compound 2 of the droplets of the active ingredient solution 1 to form a further monomolecular—outer—layer thereof, in order to produce the bilayer composed of two monomolecular layers of the first amphiphilic compound 2, i.e. in order to form finished liposomes L from the pre-liposomes M. The outer layer of the bilayer of the first amphiphilic compound 2 has an opposite orientation from the inner layer, meaning that the nonpolar regions of the first amphiphilic compound 2 of the outer layer point in the direction of the polar regions of the inner layer, i.e. in the direction of the encapsulated hydrophilic active ingredient solution 1 now encapsulated in a liposome L, whereas the polar regions of the outer layer of the bilayer point in the direction of the—hydrophilic—liquid phase 5 surrounding the liposome L.

Since the pre-liposomes M formed from the droplets of the (hydrophilic) active ingredient solution 1 with the inner layer of the first amphiphilic compound 2 accumulated thereon have a lower density than the surrounding (hydrophobic) first liquid 3 of the first emulsion 4, they experience a force acting in the direction of the arrows $P_1$ in the centrifugal field, which accelerates them in centripetal direction and brings them to the phase boundary 6 covered with a very substantially monomolecular layer of the first amphiphilic compound 2. The pre-liposome M is pushed against this layer of the first amphiphilic compound 2 enriched at this phase boundary 6 such that the monomolecular layer of the first amphiphilic compound 2 enriched at the phase boundary 6 adjoins the inner layer of the first amphiphilic compound 2 accumulated on the droplets of the active ingredient solution 1, and the bilayer of the finished liposome L is formed through hydrophobic interaction of two monomolecular layers, which is in dispersed form in the (hydrophilic) liquid phase 5 in the centrifugal field after further movement in the direction of the arrows $P_1$. In the case of a primarily ball-shaped or spherical envelope, the droplet of the active ingredient solution 1 or the pre-liposome M consequently gives rise to a symmetric liposome L having both an inner and an outer layer of the first amphiphilic compound 2 in the bilayer that forms its membrane. At the same time, it should be pointed out here that, rather than a (single) first amphiphilic compound 2, it is of course also possible to use a mixture of such compounds, for example a mixture of multiple lipids, which then respectively form the inner and outer layers of the bilayer of the liposome L.

After more or less complete formation of liposomes L, it is finally possible to separate the liquid phase 5 in which the liposomes L are dispersed from the first liquid 3, which is possible in a simple manner because the miscibility of the hydrophilic liquid phase 5 with the hydrophobic first liquid 3 is very sparing at most, and because of the different density.

For the reasons mentioned above, it is additionally possible that the first emulsion 4 is cooled to a temperature between the melting point of the (hydrophobic) first liquid 3 and the melting point of the (hydrophilic) active ingredient solution 1, in order to convert the active ingredient solution 1 of the droplets emulsified in the first liquid 3 with the monomolecular inner layer of the first amphiphilic compound 2 accumulated thereon to the solid state, after which the first emulsion 4 in the solid state of the droplets of the active ingredient solution 1 is contacted with the (hydrophilic) liquid phase 5 to form the phase boundary 6, and the first emulsion 4 and the liquid phase 5 that are in contact with one another via the phase boundary 6 are centrifuged, especially keeping the droplets of the active ingredient solution 1 constantly in the solid state of matter.

In addition, it is possible, for example, where required to modify the finished liposomes L with polymer conjugates, for example those based on polyethylene glycol (PEG), by attaching them by electrostatic means, for example, to the first amphiphilic compound 2 of the outer layer of the bilayer (not shown).

FIG. 2, in which components corresponding to FIG. 1 have been given the same reference numerals, shows a situation during the formation of primarily asymmetric liposomes in a second embodiment of a method of the invention for encapsulating active ingredients in liposomes L by an enlarged detail view in a highly schematized manner. What can be seen here in the top right-hand section of FIG. 2—insofar as analogously to the right-hand section of FIG. 1—is a droplet, for example having a diameter between about 0.1 μm and about 200 μm, of an active ingredient solution 1, which has been produced by dissolving the active ingredient in a solvent beforehand according to step (a). The solvent in the present case is, for example, a hydrophilic water- and/or alcohol-based solvent.

As additionally apparent in the top right-hand section of FIG. 2, a monomolecular (inner) layer of a first amphiphilic compound 2, for example a lipid, has been accumulated on the droplets of the active ingredient solution 1 to form a pre-liposome M, and the polar regions of the first amphiphilic compound 2 have become aligned in the direction of the hydrophilic active ingredient solution 1, and the nonpolar regions in the direction of a first liquid 3—hydrophobic here—having zero or only sparing miscibility with the solvent surrounding the droplets of the active ingredient solution 1. For production of a first emulsion 4 in such a form, the disperse phase of which is formed by the droplets of the hydrophilic active ingredient solution 1 and the continuous phase of which is formed by the hydrophobic first liquid 3, a mixture of the active ingredient solution 1 and the first amphiphilic compound 2, for example, has first been produced beforehand in step (b), and then this mixture has been dispersed into the first liquid 3 to obtain the first emulsion 4. The—hydrophobic—first liquid 3, which, in the present case, is a liquid halogenated hydrocarbon, for example, in the form of one or more fluorocarbons has been selected here such that the solubility of the first amphiphilic compound 2 is less than $10^{-4}$ mol/l— here less than $10^{-3}$ mol/l (see further details below). In addition, the first liquid 3 has preferably also been selected such that it has a lower melting point than the active ingredient solution 1 emulsified in the first emulsion 4 (likewise see further details below). The—hydrophobic—first liquid 3 also has a different density than the active ingredient solution 1, where the fluorocarbon used in the present case has a higher density than the aqueous and/or alcoholic active ingredient solution 1. At the same time, it is of course also possible in principle to use a "lighter" first liquid 3 compared to the active ingredient solution 1, i.e. one having comparatively lower density.

As apparent from the bottom left-hand section of FIG. 2, in addition, a mixture 7 of a liquid phase—hydrophilic here—having zero or sparing miscibility with the first liquid 3 of the first emulsion 4 with a second amphiphilic compound 8, for example again in the form of a lipid, has been provided in step (c), wherein the liquid phase of this mixture 7, for example, may again be chosen to correspond to the solvent of the active ingredient solution 1 and consequently, for example, may likewise be aqueous and/or alcoholic. The mixture 7 in the present case is a second emulsion 9 composed of the liquid phase of the mixture 7 and a second liquid 10—hydrophobic here—of zero or sparing miscibility therewith and the second amphiphilic compound 8, which has been produced by emulsifying the second (hydrophobic) liquid 10 in the (hydrophilic) liquid phase of the mixture 7 in the presence of the second amphiphilic compound 8, such that the continuous phase of the second emulsion 9 is formed by the (hydrophilic) liquid phase, and the disperse phase of the second emulsion 9 by the (hydrophobic) second liquid 10, which may especially be chosen to correspond to the (hydrophobic) first liquid 3 of the first emulsion 4. In this way, a monomolecular layer of the second amphiphilic compound 8 has been accumulated on the droplets of the (hydrophobic) second liquid 10 emulsified in the (hydrophilic) liquid phase of the mixture 7, and the second amphiphilic compound 8 has consequently been immobilized on these droplets to form amphiphile carriers M'.

As is additionally apparent from all four sections of FIG. 2, the first emulsion 4 composed of the first hydrophobic liquid 3 with the pre-liposomes M composed of the droplets of the active ingredient solution 1 emulsified therein and having the monomolecular (inner) layer of the first amphiphilic compound 2 accumulated thereon from step (b) has been contacted with the second emulsion 9 composed of the hydrophilic liquid phase, in which there are emulsified the amphiphile carriers M' composed of the droplets of the hydrophobic second liquid 10 and having the second amphiphilic compound 8 accumulated thereon, after which a phase boundary 6 has formed between the first liquid 3, i.e. the continuous phase of the first emulsion 4, and the liquid phase, i.e. the continuous phase of the second emulsion 9, owing to the sparing mutual miscibility thereof. The second amphiphilic compound 8 that has been added in excess to the second emulsion 9 for this purpose has been enriched here at this phase boundary 6, and, on account of the low solubility thereof in accordance with the invention in the first liquid 3 of the first emulsion 4 of less than $10^{-4}$ mol/l, there has nevertheless been no formation of an organogel as a result of excessive accumulation of the first amphiphilic compound 2 at the phase boundary 6; instead, it takes up only one or a few molecular layers. The enrichment of the first amphiphilic compound 2, the solubility of which in the first liquid 3 of the first emulsion 4 is likewise less than $10^{-4}$ mol/l, at the phase boundary 6 is very small at most since the proportion of the first amphiphilic compound 2 has firstly been adjusted in such a way that it has been very substantially accumulated as a monomolecular inner layer at the droplets of the active ingredient solution 1; secondly, the very low solubility of the first amphiphilic compound 2 in the first liquid 3 of the first emulsion 4 prevents excessive accumulation thereof at the phase boundary 6 or even the formation of an organogel.

Step (e) of the method finally envisages centrifugation of the first emulsion 4 and the second emulsion 9 that are in contact with one another via the phase boundary 6, in order firstly to transfer the droplets of the active ingredient solution 1 present in the first emulsion 4 with the monomolecular inner layer of the first amphiphilic compound 2 accumulated thereon in the direction of the arrows $P_1$ from the first liquid 3 of the first emulsion 4 through the phase boundary 6 with the molecules of the second amphiphilic compound 8 enriched thereon into the liquid continuous phase of the second emulsion 9, wherein, when it passes through the phase boundary 6, the second amphiphilic compound 8 is accumulated on the monomolecular inner layer of the first amphiphilic compound 2 of the droplets of the active ingredient solution 1 to form a further monomolecular—outer—layer thereof, in order to produce the bilayer composed of two monomolecular layers, namely firstly of the first amphiphilic compound 2 (inner layer) and secondly of the second amphiphilic compound 8 (outer layer), i.e. in order to form the finished liposomes L from the pre-liposomes M. The outer layer of the bilayer of the second amphiphilic compound 8 has an opposite orientation from the inner layer composed of the first amphiphilic compound 2, i.e. the nonpolar regions of the second amphiphilic compound 8 of the outer layer point in the direction of the polar regions of the first amphiphilic compound 2 of the inner layer, i.e. in the direction of the hydrophilic active ingredient solution 1 now encapsulated in a liposome L, while the polar regions of the second amphiphilic compound 8 of the outer layer of the bilayer point in the direction of the—hydrophilic—liquid phase of the second emulsion 9 surrounding the liposome L (in this regard see the two upper sections of FIG. 2).

Since the pre-liposomes M composed of the droplets of the (hydrophilic) active ingredient solution 1 with the inner layer of the first amphiphilic compound 2 accumulated thereon have a lower density than the surrounding (hydrophobic) first liquid 3 of the first emulsion 4, they experience a force acting in the direction of the arrows $P_1$ in the centrifugal field, which accelerates them in centripetal direction and brings them to the phase boundary 6 covered with an at least monomolecular layer of the second amphiphilic compound 8. The pre-liposome M is pushed against this layer of the second amphiphilic compound 8 enriched at the phase boundary 6 with such a force that the monomolecular layer of the second amphiphilic compound 8 enriched at the phase boundary 6 adjoins the inner layer of the first amphiphilic compound 2 accumulated on the droplets of the active ingredient solution 1, and hydrophobic interaction of two monomolecular layers gives rise to the bilayer of the finished liposome L, which, after further movement in the direction of the arrows $P_1$, is dispersed in the (hydrophilic) liquid phase of the second emulsion 9 in the centrifugal field. In the case of a primarily ball-shaped or spherical shell, the droplets of the active ingredient solution 1 or the pre-liposome M consequently forms a liposome L having, in the bilayer that forms its membrane, firstly an inner layer of the first amphiphilic compound 2 and secondly an outer layer of the second amphiphilic compound 8. Consequently, it is firstly possible to produce symmetric liposomes L when the first amphiphilic compound 2 is chosen to correspond to the second amphiphilic compound 8; secondly, it is especially possible to produce asymmetric liposomes L when the first amphiphilic compound 2 is chosen differently than the second amphiphilic compound 8. At the same time, it should be pointed out here that, rather than a (single) first amphiphilic compound 2 and/or second amphiphilic compound 8, it is of course also possible to use a mixture of such compounds, for example a mixture of multiple lipids, which then respectively form the inner and outer layers of the bilayer of the liposome L (in this regard likewise see the two upper sections of FIG. 2).

As also apparent from the two lower sections of FIG. 2, the centrifuging of the first emulsion 4 and the second emulsion 9 that are in contact with one another via the phase boundary 6 constantly transfers the droplets of the second liquid 10 with the monomolecular layer of the second amphiphilic compound 8 accumulated thereon, i.e. the amphiphile carriers M', from the liquid phase of the second emulsion 9 in the direction of the arrows $P_2$ to the phase boundary 6 between the first emulsion 4 and the second emulsion 9, in order to constantly enrich the second amphiphilic compound 8 at the phase boundary 6 in the centrifugal field, where, as a result of the accumulation elucidated in the paragraph above, it is consumed as the outer layer on the pre-liposomes M to form the liposomes L.

Since the amphiphile carriers M' composed of the droplets of the (hydrophobic) second liquid 10 with the second amphiphilic compound 8 accumulated thereon have a higher density than the surrounding (hydrophilic) liquid phase of the second emulsion 9, they experience a force that acts in the direction of the arrows $P_2$ in the centrifugal field, which accelerates them in centrifugal direction and brings them to the phase boundary 6. As they do so, they shed their monomolecular layer of the second monomolecular compound 8 as they pass into the first (hydrophobic) liquid 3, i.e. into the continuous phase of the first emulsion 4, at the phase boundary 6. In this way, the layer of the second amphiphilic compound 8 deposited at the phase boundary 6 is constantly renewed as a result of the phase transfer of the droplets of the second (hydrophobic) liquid, or the second amphiphilic compound 8 is continuously "replenished" at the phase boundary 6, whereas it is continuously consumed as the outer layer by the above-described accumulation to form the liposomes L.

After more or less complete formation of the liposomes L or after more or less complete consumption of the amphiphile carriers M' composed of the second liquid 10 with the second amphiphilic compound 8 accumulated thereon that were originally provided in the second emulsion 9, it is ultimately possible to separate the liquid phase in which the liposomes L are dispersed from the first liquid 3, which is possible in a simple manner because the miscibility of the hydrophilic liquid phase with the hydrophobic first liquid 3 is very sparing at most, and because of their different density.

For the reasons mentioned above, it is additionally possible that the first emulsion 4 is cooled down to a temperature between the melting point of the (hydrophobic) first liquid 3 and the melting point of the (hydrophilic) active ingredient solution 1, in order to convert the active ingredient solution 1 of the droplets having the monomolecular inner layer of the first amphiphilic compound 2 accumulated thereon that are emulsified in the first liquid 3 into the solid state, after which the first emulsion 4 in the solid state of the droplets of the active ingredient solution 1 is contacted with the (hydrophilic) liquid phase of the second emulsion 9, i.e. with the continuous phase thereof, to form the phase boundary 6, and the first emulsion 4 and the second emulsion 9 that are in contact with one another via the phase boundary 6 are centrifuged, especially keeping the droplets of the active ingredient solution 1 constantly in the solid state of matter.

In addition, it is firstly possible if required to modify the finished liposomes L with polymer conjugates, for example those based on polyethylene glycol (PEG), for example by attaching them electrostatically to the second amphiphilic compound 8 of the outer layer of the bilayer (not shown). Secondly, the second embodiment of the method of the invention especially offers the option that the second amphiphilic compound 8 used, which forms the monomolecular outer layer of the bilayer of liposomes L, is one or more lipids, where polymer conjugates have already been attached beforehand to at least some molecules of these lipids.

While the embodiments of a method of the invention for encapsulation of active ingredients in symmetric or asymmetric liposomes L that has been elucidated above with reference to FIGS. 1 and 2 can in principle be performed in a batchwise or else semicontinuous manner as mentioned above, the invention especially opens up the option of a continuous performance, which is consequently particularly advantageous on the industrial scale, of the two embodiments of the method.

FIG. 3 shows a schematic cross-sectional view of one embodiment of a centrifuge device suitable for continuous performance of the method of encapsulation of active ingredients in liposomes, wherein FIG. 3, for reasons of illustration, shows only half the cross section of the essentially rotationally symmetric centrifuge device. The flow-operated continuous centrifuge device shown in FIG. 3 is rotatable about its longitudinal center axis 11, and the centrifugal field that can be generated thereby is indicated by the arrows $P_3$. The centrifuge device comprises a centrifuge chamber 13 which is bounded by a circumferential wall 12 and extends over the majority of its axial length. On its left-hand side in FIG. 3, the centrifuge device has two separate inlets 14, 15 that are disposed, for example, essentially coaxially to one another. The first inlet 14 opens into a radially outer circumferential section of the centrifuge chamber 13, while the second inlet 15 opens into a radially inner central section of the centrifuge chamber 13. In the inlet region (on the left in FIG. 3) of the centrifuge device, for this purpose, there is an inlet weir 16 that extends essentially in radial direction thereof, which leaves clear firstly a radially outer, for example approximately annular, passage orifice between the first inlet 14 and the radially outer section of the centrifuge chamber 13, and secondly a radially inner, for example roughly circular, passage orifice between the second inlet 15 and the radially inner section of the centrifuge chamber 13, such that fluid media applied simultaneously to the first inlet 14 and the second inlet 15, by means of the inlet weir 16, are at first kept separate from one another, after which, as a result of the passage through the inlet weir 16, they are transferred into the common centrifuge chamber 13 on the radial outside on the one hand and on the radial inside on the other hand, specifically into the radially outer section thereof on the one hand and into the radially inner section thereof on the other hand.

On its right-hand side in FIG. 3, the centrifuge device has two separate outlets 17, 18, again arranged essentially coaxially to one another, for example. The first outlet 17 opens out from the radially outer circumferential section of the centrifuge chamber 13, while the second outlet 18 opens out from the radially inner central section of the centrifuge chamber 13. In the outlet region (on the right in FIG. 3) of the centrifuge device, for this purpose, there is an outlet weir 19 that extends essentially in radial direction thereof, which leaves clear firstly a radially outer, for example roughly annular, passage orifice between the first outlet 17 and the radially outer section of the centrifuge chamber 13, and secondly a radially inner, for example roughly circular, passage orifice between the second outlet 18 and the radially inner section of the centrifuge chamber 13, such that two fluid media of different density being centrifuged within the centrifuge chamber 13, which have especially zero or only sparing miscible with one another, after passing through the outlet weir 19, are separated from one another on the radial inside on the one hand and on the radial outside on the other hand, after which they are transferred into the first outlet 17 on the one hand and into the second outlet 18 on the other hand, in order to remove them from the centrifuge device.

In the centrifuge chamber 13, in the region of the section on the outlet side thereof, but upstream of the outflow weir 19, there is also a first retaining weir 20 that extends essentially in radial direction thereof, which is configured essentially in the form of a circular ring, for example, and extends from the outer circumferential wall 12 of the centrifuge device inward by a radial distance $R_1$, where this radial distance $R_1$, i.e. the radial width of the first retaining weir 20, appropriately corresponds at least to the radial width of the passage orifice between the radially outer end of the outlet weir 19 and the circumferential wall 12, or preferably at least slightly exceeds it. In addition, in the centrifuge chamber 13, in the region of the section on the outlet side thereof, but once again upstream of the outlet weir 19, there is a second retaining weir 21 that likewise extends essentially in radial direction thereof, which, in the present case, is in the form of a circular ring, for example, and extends between a section of the centrifuge chamber 13 which is roughly in the middle in radial terms to close to the central axis of rotation 11 of the centrifuge device, although it may instead also be of essentially circular configuration and consequently may have no central passages (not shown). The radial distance $R_2$ of the second retaining weir from the central axis of rotation 11, i.e. the radial width of the second retaining weir 21, appropriately corresponds at least to the radial width of the passage orifice between the radially inner end of the outlet weir 19 and the central axis of rotation 11, or preferably exceeds it at least slightly.

For continuous performance of the embodiments of the method of the invention described above with reference to FIGS. 1 and 2, firstly, the first emulsion 4 from step (b), wherein the hydrophobic first liquid has a higher density than the hydrophilic liquid phase 5 (FIG. 1) or than the hydrophilic continuous phase of the second emulsion 9 (FIG. 2), is supplied continuously to the first (radially outer) inlet 14 of the centrifuge device; secondly, the hydrophilic liquid phase 5 (FIG. 1) or the second emulsion 9 (FIG. 2) is supplied continuously to the second (radially inner) inlet 15 of the centrifuge device. In this case, the first emulsion 4 on the one hand and the hydrophilic liquid phase 5 (FIG. 5) or the second emulsion 9 (FIG. 2) on the other hand are first kept separate from one another by the inlet weir 16 in the inlet region of the centrifuge device, and subsequently, as soon as they have passed through the inlet weir 16 through its radially outer passage orifice on the one hand and through its radially inner passage orifice on the other hand, enter the radially outer section on the one hand and the radially inner section on the other hand of the common centrifuge chamber 13, by way of which they are contacted with one another in step (d) and the phase boundary 6 is formed. A further function of the inlet weir 16 over or under which flow may pass is to not blanket the (radially outer) inlet region of the first emulsion 4 into the centrifuge chamber 13 with the hydrophilic liquid phase 5 (FIG. 1) or with the second emulsion 9 (FIG. 2) having comparatively lower density, in order that no uncontrolled bilayers of the active ingredient solution droplets 1 with the monomolecular layer of the first amphiphilic compound 2 accumulated thereon that are present in the first emulsion 4 (cf. FIGS. 1 and 2) are generated.

In the centrifuge chamber 13, through which the flow direction is axial, i.e. from left to right in FIG. 3, the centrifuging step (e) elucidated specifically above with reference to FIGS. 1 and 2 also takes place, wherein the droplets of the active ingredient solution 1 with the monomolecular (inner) layer of the first amphiphilic compound 2 of the first emulsion 4 accumulated thereon that are emulsified in the first liquid 3 (cf. also FIGS. 1 and 2) can be accumulated in the centrifuge chamber 13 by means of the first retaining weir 20. One function of the first retaining weir 20 is consequently also that the emulsified droplets of the active ingredient solution 1 provided with a monolayer of the first amphiphilic compound 2 in the first emulsion 4 that have not yet been converted to a liposome L provided with a bilayer are not entrained out of the centrifuge chamber 13 via the first outlet 17, but reach the phase boundary 6 beforehand by virtue of buoyancy forces, in order to be able to be very substantially converted there to the liposomes L having a bilayer.

If, in accordance with the second embodiment of the method of the invention outlined with reference to FIG. 2, in step (c), a second emulsion 9 composed of the hydrophilic liquid phase with the droplets of the hydrophobic second liquid 10 that have been provided with a monomolecular layer of the second amphiphilic compound 8 emulsified therein is used, these droplets may be accumulated in the centrifuge chamber 13 by means of the second retaining weir 21. One function of the second retaining weir 21 in this case is consequently primarily that the emulsified droplets of the second hydrophobic liquid 10 provided with a monolayer of the second amphiphilic compound 8 in the second emulsion 9 which has not yet separated out the second amphiphilic compound 8 at the phase boundary 6 are not entrained out of the centrifuge chamber 13 via the second outlet 18, but reach the phase boundary 6 beforehand by virtue of the centrifugal forces induced, in order to very substantially enrich the second amphiphilic compound 8 there.

Finally, firstly the hydrophilic liquid phase 5 comprising liposomes provided with the bilayer composed of the two monomolecular layers of the first amphiphilic compound 2 (FIG. 1) or the continuous hydrophilic liquid phase of the second emulsion 9 comprising the liposomes L provided with the bilayer composed of the first amphiphilic compound 2 (inner layer) and the second amphiphilic compound 8 (outer layer) (FIG. 2), and secondly the hydrophobic first liquid 3 are separated from one another by means of the outlet weir 19 from the common centrifuge chamber 13, and withdrawn from the centrifuge device firstly via the second outlet 18 and secondly via the first outlet 17. In FIG. 3, the liquid fill levels within the centrifuge chamber 13 that can be established by means of the weirs over and under which the flows can pass can be seen. The (lighter phase) having lower density—here the hydrophilic liquid phase 5 (FIG. 1) or the continuous hydrophilic liquid phase of the second emulsion 9 (FIG. 2)—flows over the outlet weir 19 here only when the liquid column of the two phases 5 and 4, or 9 and 4, generates the same hydrostatic pressure up to the radially inner end of the outlet weir 19 as the liquid column of the "heavy" phase having comparatively higher density—the hydrophobic first liquid 3 of the first emulsion 4 here—up to the radially inner end 17*a* of the first outlet 17. One function of the outlet weir 19 over or under which the flows can pass is thus primarily to ensure complete separation of the phases 5 and 4, or 9 and 4, where the distance of the phase boundary 6 from the radially outer end of the outlet weir 19 should advantageously be adjusted such that the phase boundary 6 is incapable of reaching the radially outer end of the outlet weir 19 even in the event of fluctuations.

The invention is elucidated in detail hereinafter by working examples.

Example 1

Production of symmetric liposomes from 10 μg/ml viscumin (mistletoe extract) in 15 mM phosphate buffer in a bilayer composed of the lipid dipalmitoylphosphatidylcholine (DPPC).

Active ingredient solution: 10 μg/ml viscumin (active ingredient) in 15 mM aqueous phosphate buffer (PP) (hydrophilic solvent), First amphiphilic compound: dipalmitoylphosphatidylcholine (DPPC), First liquid (hydrophobic): perfluoroperhydrophenanthrene ($C_{14}F_{24}$, CAS number 306-91-2), Liquid phase (hydrophilic): 15 mM aqueous phosphate buffer (PP), Solubility of DPPC in $C_{14}F_{24}$: $<10^{-5}$ mol/l (detection limit).

(a) Providing the Active Ingredient Solution:

The active ingredient viscumin is dissolved in a proportion of 10 μg/ml in 15 mM aqueous phosphate buffer (PP) as hydrophilic solvent, in order to provide the hydrophilic active ingredient solution.

(b) Providing the First Emulsion:

150 mM of dipalmitoylphosphatidylcholine (DPPC) as the first amphiphilic compound is dissolved in ethanol in a round-bottom flask, and then the ethanol is fully evaporated by means of a rotary evaporator and subsequent placing of the round-bottom flask in a desiccator, such that the DPPC remains in the round-bottom flask as a dry film.

The hydrophilic active ingredient solution composed of 10 μg/ml in 15 mM PP from step (a) is then added to the round-bottom flask containing the DPPC, in order to obtain a mixture of 150 mM DPPC in the active ingredient solution.

The DPPC (first amphiphilic compound) is leached away here from the glass wall of the round-bottom flask as a result of swelling in the hydrophilic active ingredient solution, and forms polydisperse amphiphilic aggregates that are comminuted by mechanical processing. For this purpose, 2 alternative methods are employed:

extrusion through 800 nm and 400 nm pores; and use of ultrasound (Hielscher UP 200S with maximum power 200 W and an ultrasound frequency of 26 kHz): 10 seconds with a proportion of 100% of the sound treatment cycle (cycle time: about 1 second) and amplitude of 50%; the initial sound treatment for the first 10 seconds is followed by sound treatment over 10 minutes with a cycle proportion of 50% and an amplitude of 40% without cooling for comminution of the amphiphilic aggregates to an average particle size of 276 nm±50 nm.

The mixture of the active ingredient solution with the suspended aggregates of DPPC (first amphiphilic compound) produced in this way is introduced into perfluoroperhydrophenanthrene (first liquid, hydrophobic) with a proportion by volume of 1%. For emulsification, the active ingredient solution comprising the DPPC as disperse phase is suspended by means of ultrasound (Hielscher UP 200S) for 10 seconds with a cycle proportion of 100% and an amplitude of 50%, followed by 10 minutes with a cycle proportion of 50% and an amplitude of 40%, without cooling. In this way, pre-liposomes are produced from the active ingredient solution droplets having a monomolecular layer of DPPC (disperse phase of the first emulsion) in perfluoroperhydrophenanthrene (first liquid, hydrophobic as continuous phase of the first emulsion) having an average particle size of 424 nm±33 nm, a particle count of 643 kcounts/s±64 kcounts/s (derived count rate) and a polydispersity index (PDI) of 0.179. The size stability of the pre-liposomes was tested over 138 minutes and changed by less than 10% within this time.

Immediately thereafter, the first emulsion comprising the pre-liposomes is aliquoted, by dispensing 0.55 ml of the first emulsion in each case in centrifuge tubes for the subsequent batchwise centrifugation (see step (e) further down).

(c) Providing the Liquid Phase (Hydrophilic) of Zero or Sparing Miscibility with the First Liquid (Perfluoroperhydrophenanthrene, Hydrophobic) of the First Emulsion:

The hydrophilic liquid phase used is 15 mM aqueous phosphate buffer (PP), corresponding to the solvent of the active ingredient solution.

(d) Contacting the First Emulsion (Continuous Phase of the First Liquid, Perfluoroperhydrophenanthrene, Hydrophobic; Disperse Phase Composed of Pre-Liposomes of the Hydrophilic Active Ingredient Solution with Monomolecular Layer of DPPC) with the Liquid Phase (15 mM PP in Water, Hydrophilic):

In order to ensure more effective centrifugation (see step (e) further down) as a result of a higher difference in density, it is preferably possible first to freeze the aliquoted fractions of the first emulsion comprising the pre-liposomes in a freezer at −24° C. for at least 4 hours. Then the hydrophobic first liquid (perfluoroperhydrophenanthrene) of the first emulsion in which the pre-liposomes are suspended is adjusted to a controlled temperature of −3° C.±0.5° C. in an ice bath with addition of salt for about 30 minutes; the hydrophilic liquid phase in step (c) (16 mM PP in water) is set to a controlled temperature of −1° C.±0.5° C. in a thermostated bath for about 30 minutes.

The first emulsion comprising the hydrophobic first liquid as continuous phase is then contacted with the hydrophilic liquid phase by pipetting about 0.55 ml of the first emulsion comprising the pre-liposomes and 0.7 ml of the hydrophilic liquid phase into a centrifuge tube, by first layering on the first emulsion, which forms the heavier phase in the present working example, and very cautiously layering the hydrophilic liquid phase thereon, which forms the lighter phase in the present working example, so as to form a phase boundary on which the DPPC can accumulate without forming an organogel. The filling of the centrifuge tube appropriately takes place in the precooled centrifuge.

(e) Centrifuging of the First Emulsion (Continuous Phase Composed of the First Liquid, Perfluoroperhydrophenanthrene, Hydrophobic; Disperse Phase Composed of Pre-Liposomes from the Hydrophilic Active Ingredient Solution with Monomolecular Layer of DPPC) and the Liquid Phase in Contact Therewith Via the Phase Boundary (15 mM PP in Water, Hydrophilic):

The centrifuge tube filled according to the above step (d) is finally centrifuged at 4000 g (corresponding to about 39 000 $m/s^2$) at a centrifuge temperature of −3° C. for 30 to 60 minutes, in the course of which the pre-liposomes composed of the first emulsion or the first liquid thereof (perfluoroperhydrophenanthrene) are transferred through the phase boundary into the liquid phase (15 mM PP in water), and the DPPC enriched at the phase boundary accumulates as a second (outer) monomolecular layer on the first (inner) monomolecular layer of DPPC, in order to form the finished liposomes.

The hydrophilic liquid phase (15 mM PP in water) with the finished liposomes suspended therein is analyzed in order to determine the size of the liposomes produced in this way. For the visualization by transmission electron microscopy (TEM, Philips CM 12 with GATAN Multiscan 400 HP camera), ammonium molybdate as hydrophilic dye is added to the hydrophilic liquid phase with the liposomes produced therein, and the sample to be examined is applied to a copper grid and dried under air and in a desiccator. The dried samples are analyzed by TEM, with the dye producing a negative stain, meaning that the ammonium molybdate reduces transmission in the purely hydrophilic areas; as a result, the liposomes remain light-colored. FIG. 4 shows a TEM image of the liposomes produced in this way, which are spherical in shape and, according to an analysis by means of photon correlation spectroscopy (PCS, Malvern Zetasizer Nano ZS90), have a particle size of 305 nm±46 nm, an average particle count of 257±17 kcounts/s (derived count rate) and a polydispersity index (PDI) of 0.915.

Example 2

Production of symmetric liposomes from 10 μg/ml viscumin (mistletoe extract) in 15 mM phosphate buffer in a bilayer composed of the lipid distearoylphosphatidylcholine (DSPC).

- Active ingredient solution: 10 μg/ml viscumin (active ingredient) in 15 mM aqueous phosphate buffer (PP) (hydrophilic solvent),
- First amphiphilic compound: distearoylphosphatidylcholine (DSPC),
- First liquid (hydrophobic): perfluoroperhydrophenanthrene ($C_{14}F_{24}$, CAS number 306-91-2),
- Liquid phase (hydrophilic): 15 mM aqueous phosphate buffer (PP),
- Solubility of DSPC in $C_{14}F_{24}$: $<10^{-5}$ mol/1 (detection limit).

The production of liposomes takes place analogously to steps (a) to (e) according to example 1 and with corresponding proportions, but with the proviso that, rather than dipalmitoylphosphatidylcholine (DPPC), distearoylphosphatidylcholine (DPPC) is used as the first amphiphilic compound. The same applies to the transmission electron microscope analysis.

FIG. 5 shows a TEM image of the liposomes produced in this manner, which are spherical in shape and, according to PCS analysis, have an average particle size of 183 nm±51 nm, a particle count of 549±140 kcounts/s (derived count rate) and a polydispersity index (PDI) of 0.9.

Example 3

Production of symmetric liposomes from 10 µg/ml viscumin (mistletoe extract) in 15 mM phosphate buffer in a bilayer composed of a mixture of lipids dioleoylphosphatidylcholine (DOPC) and cholesterol in a molar ratio of 60:40.
Active ingredient solution: 10 µg/ml viscumin (active ingredient) in 15 mM aqueous phosphate buffer (PP) (hydrophilic solvent), First amphiphilic compound: dioleoylphosphatidylcholine (DOPC) and cholesterol in a ratio of 60:40 mol %, First liquid (hydrophobic): perfluoroperhydrophenanthrene ($C_{14}F_{24}$, CAS number 306-91-2), Liquid phase (hydrophilic): 15 mM aqueous phosphate buffer (PP), Solubility of DOPC in $C_{14}F_{24}$: $<10^{-5}$ mol/1 (detection limit), Solubility of cholesterol in $C_{14}F_{24}$: $<10^{-5}$ mol/1 (detection limit).

The production of liposomes takes place analogously to steps (a) to (e) according to example 1 and with corresponding proportions, but with the proviso that, rather than dipalmitoylphosphatidylcholine (DPPC), a mixture of dioleoylphosphatidylcholine (DOPC) and cholesterol with a molar ratio of 60:40 is used as the first amphiphilic compound. The same applies to the transmission electron microscope analysis.

FIG. 6 shows a TEM image of the liposomes produced in this manner, which are spherical in shape and, according to PCS analysis, have an average particle size of 108 nm±31 nm, a particle count of 1116±32 kcounts/s (derived count rate) and a polydispersity index (PDI) of 0.962.

Example 4

Production of symmetric liposomes from pyranin-(8-hydroxy-1,3,5-pyrenetrisulfonic acid trisodium salt (HPTS) in 15 mM phosphate buffer in a bilayer of a mixture of egg lecithin having a phosphatidylcholine content of 80% (E80) and cholesterol in a molar ratio of 60:40.

Active ingredient marker solution: Pyranin-8-hydroxy-1,3,5-pyrenetrisulfonic acid trisodium salt (HPTS) (surrogate) in 15 mM aqueous phosphate buffer (PP) (hydrophilic solvent), First amphiphilic compound: egg lecithin with a phosphatidylcholine content of 80% (E80) and cholesterol in a ratio of 60:40 mol %, First liquid (hydrophobic): perfluoroperhydrophenanthrene ($C_{14}F_{24}$, CAS number 306-91-2), Liquid phase (hydrophilic): 15 mM aqueous phosphate buffer (PP), Solubility of E80 in $C_{14}F_{24}$: $<10^{-5}$ mol/l (detection limit), Stability of cholesterol in $C_{14}F_{24}$: $<10^{-5}$ mol/l (detection limit).

(a) Providing the Active Ingredient Marker Solution:

The active ingredient marker HPTS (surrogate) is dissolved in 15 mM of aqueous phosphate buffer (PP) as hydrophilic solvent, in order to provide the hydrophilic active ingredient marker solution.

(b) Providing the First Emulsion:

The providing of the first emulsion takes place analogously to step (b) of example 1, except that the first amphiphilic compound used, rather than 150 mM DPPC, is 150 mM of a mixture of E80 and cholesterol in a molar ratio of 60:40 mol %.

In addition, in a departure from step (b) of example 1, the first emulsion comprising the pre-liposomes is aliquoted to volumes of 30 ml.

(c) Providing the Liquid Phase of Zero or Sparing Miscibility with the First Liquid (Perfluoroperhydrophenanthrene, Hydrophobic) of the First Emulsion:

The hydrophilic liquid phase provided, analogously to step (c) of example 1, is 15 mM aqueous phosphate buffer (PP), corresponding to the solvent of the active ingredient marker solution.

(d) Contacting the First Emulsion (Continuous Phase) of the First Liquid, Perfluoroperhydrophenanthrene, Hydrophobic; Disperse Phase Composed of Pre-Liposomes of the Hydrophilic Active Ingredient Marker Solution with a Monomolecular Layer of E80/Cholesterol) with the Liquid Phase (15 mM PP in Water, Hydrophilic):

The volumes of 30 ml of the first emulsion comprising the pre-liposomes that have been aliquoted as per step (b) above are used uncooled at room temperature and contacted with the hydrophilic liquid phase according to step (e) below in a flow-operated, continuous centrifuge device, as specifically elucidated above with reference to FIG. 3, forming a phase boundary at which the mixture of E80 and cholesterol can be enriched without forming an organogel.

(e) Centrifuging the First Emulsion (Continuous Phase Composed of the First Liquid, Perfluoroperhydrophenanthrene, Hydrophobic; Disperse Phase Composed of Pre-Liposomes of the Hydrophilic Active Ingredient Marker Solution with Monomolecular Layer of E80/Cholesterol) and the Liquid Phase that has been Contacted Therewith Via the Phase Boundary (15 mM PP in Water, Hydrophilic):

First of all, the dead volume of the continuous centrifuge at 333 g (corresponding to about 3300 m/$s^2$) is filled by continuous injection of firstly about 13 ml of the first emulsion (hydrophobic first liquid, perfluoroperhydrophenanthrene, with the pre-liposomes suspended therein) at a flow rate of about 1 ml/min, and secondly of the hydrophilic liquid phase (15 mM PP in water). Once the centrifuge chambers overflow, the two phases (hydrophilic/hydrophobic) are supplied continuously at a flow rate of about 0.3 ml/min, and centrifugation is continued at 333 g, with transfer of the pre-liposomes from the first emulsion or the first liquid thereof (perfluoroperhydrophenanthrene) through the phase boundary into the liquid phase (15 mM PP in water) and accumulation of the E80/cholesterol enriched at the phase boundary as the second (outer) monomolecular layer on the first (inner) monomolecular layer of E80/cholesterol, in order to form the finished liposomes. The total volumes of the two phases (hydrophilic/hydrophobic) are about 30 ml. On conclusion of the continuous supply of the two phases (hydrophilic/hydrophobic) after about 70 min., the two phases are centrifuged at 333 g for a further 20 minutes. The phases that flow out via the outlet weirs (cf. FIG. 3) are collected.

The hydrophilic liquid phase (15 mM PP in water) with the finished liposomes suspended therein is determined analogously to example 1 by means of photon correlation spectroscopy (PCS) in order to determine the size of the liposomes produced in this way. The liposomes produced in this way are of spherical shape and have an average particle size of 254 nm±3 nm, a particle count of 645 kcounts/s±6 kcounts/s (derived count rate) and a polydispersity index (PDI) of 0.380.

Example 5

Production of asymmetric liposomes from 10 µg/ml viscumin (mistletoe extract) in 15 mM of phosphate buffer in a bilayer composed firstly of a mixture of egg lecithin having a phosphatidylcholine content of 80% (E80) and cholesterol in a molar ratio of 60:40 (inner molecular layer) and secondly a mixture of egg lecithin having a phosphatidylcholine content of 80% (E80) and cholesterol in a molar ratio of 80:20 (outer monomolecular layer).

Active ingredient solution: 10 µg/ml viscumin (active ingredient) in 15 mM aqueous phosphate buffer (PP) (hydrophilic solvent),
First amphiphilic compound: egg lecithin having a phosphatidylcholine content of 80% (E80) and cholesterol in a ratio of 60:40 mol %,
Second amphiphilic compound: egg lecithin having a phosphatidylcholine content of 80% (E80) and cholesterol in a ratio of 80:20 mol %,
First liquid (hydrophobic): perfluoroperhydrophenanthrene ($C_{14}F_{24}$, CAS number 306-91-2),
Second liquid (hydrophobic): perfluoroperhydrophenanthrene ($C_{14}F_{24}$, CAS number 306-91-2),
Liquid phase (hydrophilic): 15 mM aqueous phosphate buffer (PP),
Solubility of E80 in $C_{14}F_{24}$: <$10^{-5}$ mol/l (detection limit),
Solubility of cholesterol in $C_{14}F_{24}$: <$10^{-5}$ mol/l (detection limit).

(a) Providing the Active Ingredient Solution:

Viscumin, the active ingredient, is dissolved with a proportion of 10 µg/ml in 15 mM aqueous phosphate buffer (PP) as hydrophilic solvent in order to provide the hydrophilic active ingredient solution.

(b) Providing the First Emulsion:

The providing of the first emulsion is accomplished analogously to step (b) according to example 1, except that the first amphiphilic compound used, rather than 150 mM DPPC, is 150 mM of a mixture of E80 and cholesterol in a molar ratio of 60:40 mol %, such that the first emulsion consists of 1% (v/v) of hydrophilic active ingredient solution (viscumin in 15 mM aqueous PP) in the first hydrophobic liquid (perfluoroperhydrophenanthrene) with a total proportion of 1.5 mM of the first amphiphilic compound (E80 and cholesterol in a ratio of 60:40 mol %).

In this way, pre-liposomes are produced from the active ingredient solution droplets having a monomolecular layer of E80/cholesterol in a molar ratio of 60:40 mol % (disperse phase of the first emulsion) in perfluoroperhydrophenanthrene (first liquid, hydrophobic as continuous phase of the first emulsion) having an average particle size of 376 nm±22 nm, a particle count of 482 kcounts/s±35 kcounts/s (derived count rate) and a polydispersity index (PDI) of 1.0.

In addition, in a departure from step (b) according to example 1, the first emulsion comprising the pre-liposomes was aliquoted to volumes of 30 ml.

(c) Providing the Mixture—Here in the Form of the Second Emulsion—of the Liquid Phase (Hydrophilic) of Zero or Sparing Miscibility with the First Liquid (Perfluoroperhydrophenanthrene, Hydrophobic) of the First Emulsion with the Second Amphiphilic Compound with the Second Liquid Emulsified Therein (Hydrophobic):

E80/Cholesterol in a molar ratio of 80:20 mol % as the second amphiphilic compound is dissolved in ethanol in a round-bottom flask, and then the ethanol is fully evaporated by means of a rotary evaporator followed by storage of the round-bottom flask in a desiccator, so as to leave the second amphiphilic compound as a dry film in the round-bottom flask.

The hydrophilic liquid phase composed of 15 mM aqueous PP is then added to the round-bottom flask containing the E80/cholesterol in a molar ratio of 80:20 mol %, in order to obtain a mixture of 150 mM E80/cholesterol in a molar ratio of 80:20 mol % (second amphiphilic compound) in 15 mM aqueous PP (hydrophilic liquid phase). The E80/cholesterol in a molar ratio of 80:20 mol % becomes detached here from the glass wall of the round-bottom flask owing to swelling in the hydrophilic active ingredient solution, and forms polydisperse amphiphilic aggregates that can be reduced in size by mechanical processing. For this purpose, it is again possible to use 2 alternative methods:

extrusion through 800 nm and 400 nm pores; and
use of ultrasound (Hielscher UP 200S with maximum power 200 W and an ultrasound frequency of 26 kHz): 10 seconds with a proportion of 100% of the sound treatment cycle (cycle time: about 1 second) and an amplitude of 50%; the initial sound treatment for the first 10 seconds is followed by sound treatment over 10 minutes with a cycle proportion of 50% and an amplitude of 40% without cooling for comminution of the amphiphilic aggregates.

Then the second emulsion is produced by dispersing the hydrophobic second liquid (perfluoroperhydrophenanthrene) into the mixture of the hydrophilic liquid phase (15 mM aqueous PP) with the suspended aggregates of E80/cholesterol in a molar ratio of 80:20 mol % (second amphiphilic compound) generated in this way with a proportion by volume of about 1%. For emulsification, the perfluoroperhydrophenanthrene as disperse phase is suspended by means of ultrasound (Hielscher UP 200S) for 10 seconds with a cycle proportion of 100% and an amplitude of 50%, followed by 30 minutes with a cycle proportion of 75% and an amplitude of 60%, without cooling, such that the second emulsion consists of 1% (v/v) hydrophobic second liquid (perfluoroperhydrophenanthrene) in the hydrophilic liquid phase (15 mM aqueous PP) with a total content of 1.5 mM of the second amphiphilic compound (E80 and cholesterol in a ratio of 80:20 mol %).

In this way, amphiphile carriers composed of the perfluoroperhydrophenanthrene droplets with a monomolecular layer of E80/cholesterol, the second amphiphilic compound, in a molar ratio of 80:20 mol % (disperse phase of the second emulsion) in 15 mM aqueous PP (liquid phase, hydrophilic as continuous phase of the second emulsion) are produced with an average particle size of 127 nm±6 nm, a particle count of 1411 kcounts/s±52 kcounts/s (derived count rate) and a polydispersity index (PDI) of 0.298.

Immediately thereafter, the second emulsion with the amphiphile carriers is also aliquoted to volumes of 30 ml.

(d) Contacting of the First Emulsion (Continuous Phase of Perfluoroperhydrophenanthrene, the First Liquid, Hydrophobic; Disperse Phase Composed of Pre-Liposomes of the Hydrophilic Active Ingredient Solution with a Monomolecular Layer of E80/Cholesterol in a Molar Ratio of 60:40 Mol %) with the Second Emulsion (Continuous Phase Composed of 15 mM PP in Water, the Liquid Phase, Hydrophilic; Disperse Phase Composed of Amphiphile Carriers Composed of Perfluoroperhydro-phenanthrene, the Second Liquid, with a Monomolecular Layer of E80/Cholesterol in a Molar Ratio of 80:20 Mol %):

The volumes of 30 ml of the first emulsion comprising the pre-liposomes that were aliquoted in step (b) above are used uncooled at room temperature and contacted in step (e) below in a flow-operated, continuous centrifugation device, as specifically elucidated above with reference to FIG. 3, with the volumes of 30 ml of the second emulsion comprising the amphiphile carriers that were aliquoted in step (c) above, for the phase boundary between the continuous phases of the first and second emulsions at which the mixture of E80 and cholesterol can accumulate without forming an organogel.

(e) Centrifuging of the First Emulsion (Continuous Phase of Perfluoroperhydrophenanthrene, the First Liquid, Hydrophobic; Disperse Phase Composed of Pre-Liposomes Composed of the Hydrophilic Active Ingredient Solution with a Monomolecular Layer of E80/Cholesterol in a Molar Ratio of 60:40 Mol %) with the Second Emulsion in Contact Therewith Via the Phase Boundary (Continuous Phase Composed of 15 mM PP in Water, the Liquid Phase, Hydrophilic; Disperse Phase Composed of Amphiphile Carriers Composed of Perfluoroperhydrophenanthrene, the Second Hydrophobic Liquid, with a Monomolecular Layer of E80/Cholesterol in a Molar Ratio of 80:20 Mol %):

First of all, the dead volume of the continuous centrifuge at 1000 g (corresponding to about 9800 m/s$^2$) is filled by continuous injection of about 13 ml firstly of the first emulsion (perfluoroperhydrophen-anthrene, hydrophobic first liquid, with the pre-liposomes suspended therein) at a flow rate of about 1 ml/min, and secondly of the second emulsion (15 mM PP in water, hydrophilic liquid phase, with the amphiphile carriers suspended therein). Once the centrifuge chambers overflow, the two phases (hydrophilic/hydrophobic) are fed in continuously at a flow rate of about 0.3 ml/min, and continuous integration continues at 1000 g. In the course of this, the amphiphile carriers from the second emulsion are first supplied continuously to the phase boundary in the centrifugal field, in order to constantly enrich the second amphiphilic compound (E80/cholesterol in a molar ratio of 80:20 mol %) at the phase boundary. Secondly, the pre-liposomes of the first emulsion or of the first liquid thereof (perfluoroperhydrophen-anthrene) are transferred through the phase boundary into the liquid phase (15 mM PP in water), with accumulation of the second amphiphilic compound enriched at the phase boundary (E80/cholesterol in a molar ratio of 80:20 mol %) as the second (outer) monomolecular layer on the first (inner) monomolecular layer of the first amphiphilic compound (E80/cholesterol in a molar ratio of 60:40), in order to form the finished liposomes. The total volumes of the two phases (hydrophilic/hydrophobic) are about 30 ml. On conclusion of the continuous supply of the two phases (hydrophilic/hydrophobic) after about 70 min., the two phases are centrifuged at 1000 g for a further 20 min. The phases that flow away via the outlet weirs (cf. FIG. 3) are collected.

The hydrophilic liquid phase (15 mM PP in water) with the finished—asymmetric—liposomes suspended therein is analyzed analogously to example 1 by means of PCS, in order to determine the average size of the liposomes produced in this way. The liposomes produced in this way, which have a different composition of the inner and outer monomolecular layer of their bilayer, are of spherical shape and have an average particle size of 367 nm±61 nm, a particle count of 3207 kcounts/s±52 kcounts/s (derived count rate) and a polydispersity index (PDI) of 0.30.

The invention claimed is:

1. A method of encapsulating active ingredients in liposomes, comprising:
   a solution of the active ingredient; and
   at least one bilayer composed of two at least monomolecular layers of at least one first amphiphilic compound;
   wherein the active ingredient solution is encapsulated by the at least one bilayer, comprising the following steps:
   (a) providing the active ingredient solution of the active ingredient to be encapsulated by dissolving the active ingredient in at least one solvent;
   (b) providing a first emulsion by emulsifying the active ingredient solution from step (a) in at least one first liquid having zero or sparing miscibility with the at least one solvent of the active ingredient solution, in the presence of the at least one first amphiphilic compound, in order to accumulate an at least monomolecular inner layer of the at least one first amphiphilic compound onto droplets of the active ingredient solution emulsified in the at least one first liquid;
   (c) providing a liquid phase having zero or sparing miscibility with the at least one first liquid of the first emulsion from step (b);
   (d) contacting the first emulsion composed of the at least one first liquid and having the droplets of the active ingredient solution that are emulsified therein and have the at least monomolecular inner layer of the at least one first amphiphilic compound that has been accumulated thereon from step (b) with the liquid phase from step (c) to form a phase boundary between the first emulsion from step (b) and the liquid phase from step (c), wherein the at least one first amphiphilic compound is enriched at the phase boundary; and
   (e) centrifuging the first emulsion from step (b) and the liquid phase from step (c) that are in contact with one another via the phase boundary, in order to transfer the droplets of the active ingredient solution present in the first emulsion and having the at least monomolecular inner layer of the at least one first amphiphilic compound that has been accumulated thereon from the at least one first liquid of the first emulsion from step (b) into the liquid phase from step (c), wherein, when the droplets of the active ingredient solution having the at least monomolecular inner layer of the at least one first amphiphilic compound that has been accumulated thereon passes the phase boundary, the at least one first amphiphilic compound enriched there is accumulated on the at least monomolecular inner layer of the at least one first amphiphilic compound of the droplets of the active ingredient solution to form an at least monomolecular outer layer thereof, in order to produce the at least one bilayer composed of the two at least monomolecular layers of the at least one first amphiphilic compound; wherein the at least one first liquid of the first emulsion from step (b) is chosen such that the solubility of the at least one first amphiphilic compound in the at least one first liquid is not more than $1 \times 10^{-4}$ mol/l.

2. The method as claimed in claim 1, wherein the at least one first liquid of the first emulsion from step (b) is chosen such that the solubility of the at least one first amphiphilic compound in the first liquid is not more than $0.5 \times 10^{-4}$ mol/l.

3. The method as claimed in claim 1, wherein the first emulsion from step (b) is created by first providing a mixture of the active ingredient solution of the active ingredient to be encapsulated from step (a) and the at least one first amphiphilic compound; and then emulsifying this mixture to form the first emulsion from step (b) in the at least one first liquid by dispersing the mixture into the at least one first liquid.

4. The method as claimed in claim 1, wherein the at least one first liquid used in the first emulsion from step (b) is selected from the group of:
   liquid, partly or wholly halogenated hydrocarbons, including fluorocarbons;
   silicone oils; and
   siloxanes;
   including mixtures thereof.

5. The method as claimed in claim 1, wherein the at least one solvent used in the active ingredient solution from step (a) is a hydrophilic solvent, wherein the first liquid used in the first emulsion of step (b) is a hydrophobic first liquid, and wherein the liquid phase provided in step (c) is a hydrophilic liquid phase.

6. The method as claimed in claim 1, wherein:
   the at least one first liquid of the first emulsion with the droplets of the active ingredient solution emulsified therein and having the at least monomolecular inner layer of the at least one first amphiphilic compound accumulated thereon from step (b) is chosen such that it has a lower melting point than the active ingredient solution;
   the first emulsion from step (b) is cooled down to a temperature between the melting point of the at least one first liquid of the first emulsion and the melting point of the active ingredient solution, in order to convert the droplets of the active ingredient solution emulsified in the at least one first liquid and having the at least monomolecular inner layer of the at least one first amphiphilic compound accumulated thereon from step (b) to a solid state; and then
   the first emulsion from step (b) in the solid state of the active ingredient solution is contacted with the liquid phase or mixture of the liquid phase with at least one second amphiphilic compound that has zero or sparing miscibility with the at least one first liquid of the first emulsion from step (b), to form the phase boundary according to step (d), and
   the first emulsion from step (b) and the liquid phase or the mixture of the liquid phase with the at least one second amphiphilic compound that are in contact with one another via the phase boundary in step (e) are centrifuged.

7. The method as claimed in claim 6, wherein the active ingredient solution having the at least monomolecular inner layer of the at least one first amphiphilic compound accumulated thereon is kept in the solid state during the centrifuging, in order to move it, on account of a resultant difference in density, from the phase boundary in the direction of the liquid phase or the mixture of the liquid phase with the at least one second amphiphilic compound.

8. The method as claimed in claim 1, wherein the at least one bilayer composed of the two at least monomolecular layers of the at least one first amphiphilic compound or the two at least monomolecular layers of the at least one first amphiphilic compound and of the at least one second amphiphilic compound is modified by reaction with hydrophilic polymer conjugates.

9. The method as claimed in claim 1 is performed:
   batchwise in a batchwise centrifugation device;
   semicontinuously in a batchwise centrifugation device; or
   continuously in a flow-operated continuous centrifugation device.

10. The method as claimed in claim 1, wherein the at least one first amphiphilic compound is selected from the group of lipids.

11. A method of encapsulating active ingredients in liposomes, comprising:
   a solution of the active ingredient; and
   at least one bilayer composed of two at least monomolecular layers of at least one first amphiphilic compound and at least one second amphiphilic compound;
   wherein the active ingredient solution is encapsulated by the at least one bilayer, comprising the following steps:
   (a) providing an active ingredient solution of the active ingredient to be encapsulated by dissolving the active ingredient in at least one solvent;
   (b) providing a first emulsion by emulsifying the active ingredient solution from step (a) in at least one first liquid, especially a hydrophobic first liquid, having zero or sparing miscibility with the at least one solvent of the active ingredient solution, in the presence of the at least one first amphiphilic compound, in order to accumulate an at least monomolecular inner layer of the at least one first amphiphilic compound on droplets of the active ingredient solution emulsified in the at least one first liquid;
   (c) providing a mixture of a liquid phase having zero or sparing miscibility with the at least one first liquid of the first emulsion from step (b) with the at least one second amphiphilic compound;
   (d) contacting the first emulsion composed of the at least one first liquid and having the droplets of the active ingredient solution that are emulsified therein and have the at least monomolecular inner layer of the at least one first amphiphilic compound that has been accumulated thereon from step (b) with the mixture of the liquid phase with the at least one second amphiphilic compound from step (c) to form a phase boundary between the first emulsion from step (b) and the mixture from step (c), wherein at least the at least one second amphiphilic compound is enriched at this phase boundary; and
   (e) centrifuging the first emulsion from step (b) and the mixture from step (c) that are in contact with one another via the phase boundary, in order to transfer the droplets of the active ingredient solution present in the first emulsion and having the at least monomolecular inner layer of the at least one amphiphilic compound that has been accumulated thereon from the at least one first liquid of the first emulsion from step (b) into the liquid phase of the mixture from step (c), wherein, when the droplets of the active ingredient solution having that at least monomolecular inner layer of the at least one first amphiphilic compound that has been accumulated thereon passes the phase boundary, the at least one second amphiphilic compound enriched there is accumulated on the at least monomolecular inner layer of the at least one first amphiphilic compound of the droplets of the active ingredient solution to form an at least monomolecular outer layer thereof, in order to produce the at least one bilayer composed of the two at least monomolecular layers of the at least one first amphiphilic compound and the at least one second amphiphilic compound;

wherein the at least one first liquid of the first emulsion from step (b) is chosen such that the solubility of the at least one first amphiphilic compound in the at least one first liquid is not more than $1\times10^{-4}$ mol/l.

12. The method as claimed in claim 11, wherein the at least one first liquid of the first emulsion from step (b) is chosen such that the solubility both of the at least one first amphiphilic compound and of the at least one second amphiphilic compound in the at least one first liquid is not more than $1\times10^{-4}$ mol/l.

13. The method as claimed in claim 11, wherein the at least one first liquid of the first emulsion from step (b) is chosen such that the solubility at least of the at least one first amphiphilic compound in the first liquid is not more than $0.5\times10^{-4}$ mol/l.

14. The method as claimed in claim 11, wherein:
the mixture of the liquid phase with the at least one second amphiphilic compound used in step (c) is a second emulsion of the liquid phase and at least one second liquid having zero or sparing miscibility therewith with the at least one second amphiphilic compound, in that the at least one second liquid is emulsified in the liquid phase in the presence of the at least one second amphiphilic compound in order to accumulate an at least monomolecular layer of the at least one second amphiphilic compound on droplets of the second liquid emulsified in the liquid phase and to immobilize the at least one second amphiphilic compound on these droplets in this way; and
on centrifugation of the first emulsion from step (b) and the mixture in the form of the second emulsion from step (c) that are in contact with one another via the phase boundary, the droplets of the at least one second liquid with the at least monomolecular layer of the at least one second amphiphilic compound accumulated thereon are constantly transferred from the liquid phase of the second emulsion to the phase boundary between the first emulsion and the second emulsion, in order to constantly enrich the at least one second amphiphilic compound at this phase boundary.

15. The method as claimed in claim 14, wherein the at least one second liquid having zero or sparing miscibility with the liquid phase of the second emulsion is chosen to correspond to the at least one first liquid, especially hydrophobic first liquid, of the first emulsion from step (b).

16. The method as claimed in claim 14, wherein the mixture in the form of the second emulsion from step (c) is created by first providing a mixture of the liquid phase from step (c) and the at least one second amphiphilic compound; and then emulsifying the second liquid in this mixture to form the second emulsion, by dispersing the at least one second liquid into this mixture.

17. The method as claimed in claim 11, wherein the first emulsion from step (b) is created by:
first providing a mixture of the active ingredient solution of the active ingredient to be encapsulated from step (a) and the at least one first amphiphilic compound; and
then emulsifying this mixture to form the first emulsion from step (b) in the at least one first liquid by dispersing the mixture into the at least one first liquid.

18. The method as claimed in claim 11, wherein the at least one first liquid used in the first emulsion from step (b) is selected from the group of:
liquid, partly or wholly halogenated hydrocarbons, including fluorocarbons;
silicone oils; and
siloxanes;
including mixtures thereof.

19. The method as claimed in claim 11, wherein the at least one solvent used in the active ingredient solution from step (a) is a hydrophilic solvent, wherein the first liquid used in the first emulsion of step (b) is a hydrophobic first liquid, and wherein the liquid phase used in the mixture of step (c) is a hydrophilic liquid phase.

20. The method as claimed in claim 11, wherein
the at least one first liquid of the first emulsion with the droplets of the active ingredient solution emulsified therein and having the at least monomolecular inner layer of the at least one first amphiphilic compound accumulated thereon from step (b) is chosen such that it has a lower melting point than the active ingredient solution;
the first emulsion from step (b) is cooled down to a temperature between the melting point of the at least one first liquid of the first emulsion and the melting point of the active ingredient solution, in order to convert the droplets of the active ingredient solution emulsified in the at least one first liquid and having the at least monomolecular inner layer of the at least one first amphiphilic compound accumulated thereon from step (b) the solid state; and then
the first emulsion from step (b) in the solid state of the active ingredient solution is contacted with the liquid phase or mixture of the liquid phase with the at least one second amphiphilic compound that has zero or sparing miscibility with the at least one first liquid of the first emulsion from step (b), to form the phase boundary according to step (d), and
the first emulsion from step (b) and the liquid phase or the mixture of the liquid phase with the at least one second amphiphilic compound that are in contact with one another via the phase boundary in step (e) are centrifuged.

21. The method as claimed in claim 11, wherein the at least one bilayer composed of:
the two at least monomolecular layers of the at least one first amphiphilic compound or the two at least monomolecular layers of the at least one first amphiphilic compound and of the at least one second amphiphilic compound is modified by reaction with hydrophilic polymer conjugates.

22. The method as claimed in claim 11 is performed:
batchwise in a batchwise centrifugation device;
semicontinuously in a batchwise centrifugation device; or
continuously in a flow-operated continuous centrifugation device.

23. The method as claimed in claim 11, wherein the at least one first amphiphilic compound and the at least one second amphiphilic compound are selected from the group of lipids.

* * * * *